United States Patent
Prisyazhnoy et al.

(10) Patent No.: US 10,065,133 B2
(45) Date of Patent: Sep. 4, 2018

(54) SEPARATION MATERIAL COMPRISING PHOSPHORYL CHOLINE DERIVATIVES

(71) Applicant: Pentracor GmbH, Henningsdorf (DE)

(72) Inventors: Victor Prisyazhnoy, Luckenwalde (DE); Stephan Mattecka, Berlin (DE); Ahmed Sheriff, Berlin (DE); Roderich Süssmuth, Berlin (DE)

(73) Assignee: Pentracor GmbH, Luckenwalde (DE)

( * ) Notice: Subject to any disclaimer, the term of this patent is extended or adjusted under 35 U.S.C. 154(b) by 0 days.

(21) Appl. No.: 15/319,782

(22) PCT Filed: Jun. 19, 2015

(86) PCT No.: PCT/EP2015/063887
§ 371 (c)(1),
(2) Date: Dec. 18, 2016

(87) PCT Pub. No.: WO2015/193504
PCT Pub. Date: Dec. 23, 2016

(65) Prior Publication Data
US 2017/0120163 A1    May 4, 2017

(30) Foreign Application Priority Data
Jun. 19, 2014 (EP) .................................. 14173195

(51) Int. Cl.
*B01D 15/38* (2006.01)
*C07F 9/10* (2006.01)
*C08B 37/00* (2006.01)
*B01J 20/24* (2006.01)

(52) U.S. Cl.
CPC .......... *B01D 15/3809* (2013.01); *B01J 20/24* (2013.01); *C07F 9/10* (2013.01); *C08B 37/0039* (2013.01); *C07B 2200/11* (2013.01)

(58) Field of Classification Search
CPC .................................................. B01D 15/3809
See application file for complete search history.

(56) References Cited

U.S. PATENT DOCUMENTS

2006/0019930 A1*  1/2006 Pepys ................ A61K 49/0004
514/91

OTHER PUBLICATIONS

Rheumatoid arthritis [online], retrieved from the internet on Jul. 7, 2017; URL: http://www.mayoclinic.org/diseases-conditions/rheumatoid-arthritis/diagnosis-treatment/treatment.*
Rheumatoid arthritis [online], retrieved from the internet on Jul. 7, 2017; URL: http://www. arthritis.org/about-arthritis/types/rheumatoid-arthritis/.*
Diabetes [online], retrieved from the internet on Jul. 7, 2017; URL: http://www.medicalnewstoday.com/info/diabetes.*

* cited by examiner

*Primary Examiner* — Shawquia Jackson
(74) *Attorney, Agent, or Firm* — Meyertons, Hood, Kivlin, Kowert & Goetzel, P.C.; Mark E. DeLuca

(57) ABSTRACT

The present invention provides phosphoryl choline derivatives of general formula (I), which are suitable to be immobilized on a solid support to provide a separation material of general formula (II), which bind with both high affinity and high specificity to a protein, more specifically to C-reactive protein and anti-phosphoryl choline antibodies. Said separation materials are particularly useful in the extracorporeal removal of C-reactive protein and anti-phosphoryl choline antibodies from a biological fluid of a patient for prophylaxis and/or treatment of immune dysfunctions and cardiovascular diseases. Also provided is a column that comprises the separation material of general formula (II), as well as a device containing the column. Formula (I), wherein variable X is selected from: —SH, —NHR$^3$, —C≡CH, —CH=CH$_2$, —N$_3$ and —CHO; the other variables are as defined in the claims: Formula (II), wherein variable "A" represents a solid support. "A" as well as the other variables are defined in detail in the claims.

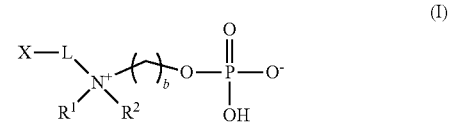

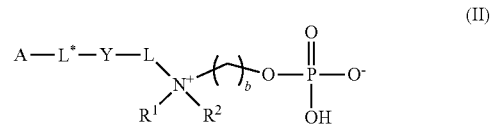

7 Claims, No Drawings

SEPARATION MATERIAL COMPRISING PHOSPHORYL CHOLINE DERIVATIVES

The present invention provides phosphoryl choline derivatives of general formula (I), which are suitable to be immobilized on a solid support to provide a separation material of general formula (II), which bind with both high affinity and high specificity to a protein, more specifically to C-reactive protein and anti-phosphoryl choline antibodies. Said separation materials are particularly useful in the extracorporeal removal of C-reactive protein and anti-phosphoryl choline antibodies from a biological fluid of a patient for prophylaxis and/or treatment of immune dysfunctions and cardiovascular diseases. Also provided is a column that comprises the separation material of general formula (II), as well as a device containing the column.

BACKGROUND OF THE INVENTION

C-reactive protein (CRP) is an acute phase reactant produced by the liver in response to cytokine release during inflammation. It has long been used in clinical practice to follow systemic inflammation, especially bacterial infection. More recently, epidemiological evidence has shown that basal levels of CRP, in the absence of apparent inflammatory disease may be informative in predicting future myocardial or cerebrovascular events (Ridker et al. *Circulation*, 2001 103, 1813). Also of interest is the fact that CRP is a potential inflammatory marker believed to be of value in the prediction of coronary events (Danesh et al. *N. Engl. J. Med.* 2004 350, 1387) and that CRP is a causative factor of the destructive processes observed during the weeks after myocardial infarction (Slagman et al., *Blood Purif.* 2011, 31, 9).

Several studies have shown the binding affinity of phosphoryl choline (PC) for CRP. Hence, PC derivatives immobilized on a solid support are widely used to isolate PC binding proteins from different biological sources. However, the most important clinical application of above mentioned PC derivatives immobilized on solid support is the extracorporeal removal of C-reactive protein and anti-phosphoryl choline antibodies from a biological fluid.

WO 90/12632 describes a method for removing CRP and anti-phosphoryl choline antibodies from biological fluids to improve the cellular immune responses thereof, and a method for removing CRP and anti-phosphoryl choline antibodies from the circulation of patients with cancer by conducting extracorporeal perfusion of a patient's blood plasma through a phosphoryl choline-matrix adsorption device so as to improve the patient's cellular immune responses against the cancer.

WO 2007/076844 describes a method for treating the risk of accumulating CRP by performing an extracorporeal perfusion of blood plasma of patients presenting a risk of cardiovascular diseases or immune dysfunctions such as autoimmune diseases by means of a column, which contains absorbent matrix material including PC derivatives to eliminate CRP from a patient's biological liquids so as to prevent and/or treat autoimmune diseases, cardiovascular diseases such as myocardial infarction, stroke, diabetes, rheumatism, and renal insufficiency.

The synthesis of PC derivative of bovine serum albumin (PC-BSA), its immobilization on Toyopearl® HW 65 and its use for CRP affinity purification was also described (Stults et al. *Anal. Biochem.* 1987, 161, 567). In this study, the immobilization of the PC derivative on the solid support was achieved via formation of a phosphodiester linkage. Others PC derivatives were in a similar manner immobilized on a solid support (Spande T. F. *J. Org. Chem.* 1980, 45, 3081; Martin, L. M. *Tetrahedron Lett.* 1996 37, 7921).

WO 2013/176084 A1 discloses also a silylalkyl phosphoramidate compound of general formula (1) for coating a medical device in order to suppress the adhesion of biological material, such as platelets.

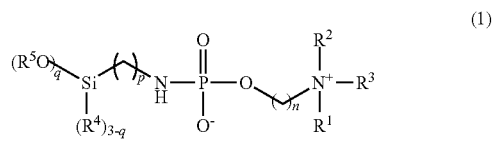
(1)

WO 2012/160187 A1 provides ammonium-containing phosphonic acid derivatives for use in the treatment of an inflammatory, autoimmune and/or allergic disorder. It is postulated that the disclosed compounds exert their pharmacological activity through inhibition of the phosphoinositide 3-kinase (PI3K)/Akt kinase pathway.

At our knowledge, up to present the immobilization of PC on solid support was achieved only via formation of a phosphodiester bond. The immobilization of PC derivatives via phosphodiester bond formation has some advantages, but also severe drawbacks. The main drawback of this approach is that formation of phosphodiester bond changes the overall charge (net charge) of the molecule of PC and thereby, alters the orientation of so modified PC in a binding pocket. In addition, a phosphodiester bond can be easily cleaved by non-specific phosphodiesterases present in the biological fluids leading to instability issues of the matrices, which were substituted in such manner.

To eliminate the aforementioned drawbacks, it is the objective of the present invention to provide compounds, which can be immobilized on a solid support to provide a separation material that bind with both high affinity and high specificity CRP for prophylaxis and/or treatment of immune dysfunctions and cardiovascular diseases by extracorporeal removal of CRP and anti-phosphoryl choline antibodies.

This objective is solved by the compounds of general formula (I) according to independent claim 1, the separation material according to independent claim 5 for use in the extracorporeal removal of CRP and anti-phosphoryl choline antibodies from a biological fluid of a patient for prophylaxis and/or treatment of immune dysfunctions and cardiovascular diseases.

The objective of the present invention is solved by the teaching of the independent claims. Further advantageous features, aspects and details of the invention are evident from the dependent claims, the description, the figures, and the examples of the present application.

DESCRIPTION OF THE INVENTION

Thus, the present invention relates to a compound of general formula (I)

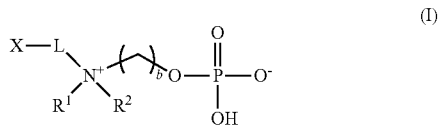
(I)

wherein
b is selected from 2 and 3;
$R^1$ and $R^2$ are independently of each other selected from: —$CH_3$, —$C_2H_5$, —$C_3H_7$, —$C_4H_9$, —$C_5H_{11}$ and —$C_6H_{13}$, or $R^1$ and $R^2$ can form together with the nitrogen atom to which they are connected a heterocycle selected from:

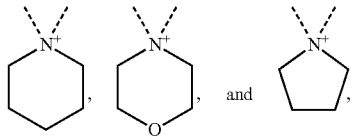

wherein one or several hydrogen atom(s) can be replaced with (a) fluorine atom(s);
X is selected from: —SH, —$NHR^3$, —C≡CH, —CH=$CH_2$, —$N_3$ and —CHO;
$R^3$ is selected from: —H, —$CH_3$, —$C_2H_5$ and —$C_3H_7$;
-L- is selected from: -$L^a$-, -$L^a$-$L^e$-, -$L^a$-$L^b$-$L^e$- and -$L^a$-$L^b$-$L^d$-$L^c$-$L^e$-, wherein
-$L^a$- is selected from: —$(CH_2)_m$—, —$(CH_2$—$CH_2$—$O)_m$—$CH_2$—,

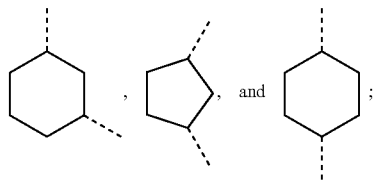

-$L^b$- and -$L^c$- are independently of each other selected from: —O—, —NH—C(O)—, —C(O)—NH—, —O—(O)—NH— and —$SO_2$—;
-$L^d$- is selected from: —$(CH_2)_n$—, —$(CH_2$—$CH_2$—$O)_n$—$CH_2$—,

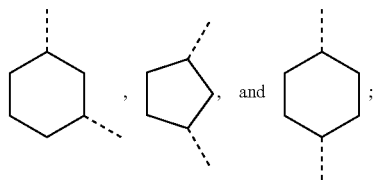

-$L^e$- is selected from: —$(CH_2)_{p1}$—, —$(CH_2)_{p1}$—O—$(CH_2)_{p2}$—,

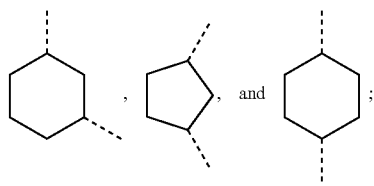

m, n, p1 and p2 are independently of each other selected from 1, 2, 3, 4, 5, 6, 7, 8, 9, 10;
and enantiomers, mixtures of enantiomers, tautomers, hydrates, solvates, racemates, protonated and deprotonated forms of the above mentioned compounds.

It is clear to the skilled person that the left extremity of the fragment -L- is connected to X and the right extremity of the fragment -L- is connected to

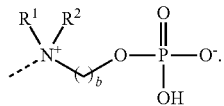

Same applies to the fragments: -$L^a$-, -$L^b$-, -$L^c$-, -$L^d$- and -$L^e$-.
Thus, for example, if -L- represents -$L^a$-$L^b$-$L^e$- with -$L^a$- being —$(CH_2)_m$—, -$L^b$- being —O—C(O)—NH—, and -$L^e$- being —$(CH_2)_{p1}$—O—$(CH_2)_{p2}$—, then the compound of general formula (I) is the following:

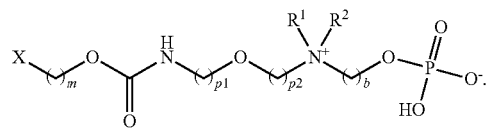

The expression tautomer as used herein refers to an organic compound that is interconvertible by a chemical reaction called tautomerization. Tautomerization is catalyzed by bases, acids or other suitable compounds.
Preferred compounds of the current invention are compounds of general formula (I):

(I)

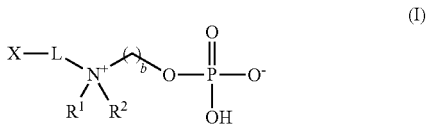

wherein b is selected from 2 and 3;
$R^1$ and $R^2$ are independently of each other selected from: —$CH_3$ and —$C_2H_5$, or
$R^1$ and $R^2$ can form together with the nitrogen atom to which they are connected, a heterocycle selected from:

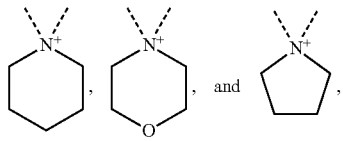

wherein one or several hydrogen atom(s) can be replaced with (a) fluorine atom(s);
X is selected from: —SH, —$NHR^3$, —C≡CH, —CH=$CH_2$, —$N_3$ and —CHO;
$R^3$ is selected from: —H, —$CH_3$, —$C_2H_5$ and —$C_3H_7$;
-L- is selected from: -$L^a$-, -$L^a$-$L^e$-, -$L^a$-$L^b$-$L^e$- and -$L^a$-$L^b$-$L^d$-$L^c$-$L^e$-, wherein
-$L^a$- represents: —$(CH_2)_m$— or —$(CH_2$—$CH_2$—$O)_m$—$CH_2$—;
-$L^b$- and -$L^c$- are independently of each other selected from: —O—, —NH—C(O)—, —C(O)—NH—, —O—C(O)—NH— and —$SO_2$—;
-$L^d$- represents: —$(CH_2)_n$— or —$(CH_2$—$CH_2$—$O)_n$—$CH_2$—;

-L$^e$- is selected from: —(CH$_2$)$_{p1}$— and —(CH$_2$)$_{p1}$—O—(CH$_2$)$_{p2}$—; and m, n, p1 and p2 are independently of each other selected from 1, 2, 3, 4, 5, 6, 7, 8, 9, 10.

A preferred embodiment according to the present invention is directed to compounds of general formula (I), wherein X is selected from: —SH, —NHR$^3$, and —CHO, and more preferably is selected from: —SH and —NHR$^3$.

Another preferred embodiment of the current invention relates to compounds of general formula (I), wherein X represents: —C≡CH, —CH═CH$_2$, or —N$_3$.

Preferred compounds of the current invention are compounds of the following general formula (III), (IV), (V) and (VI):

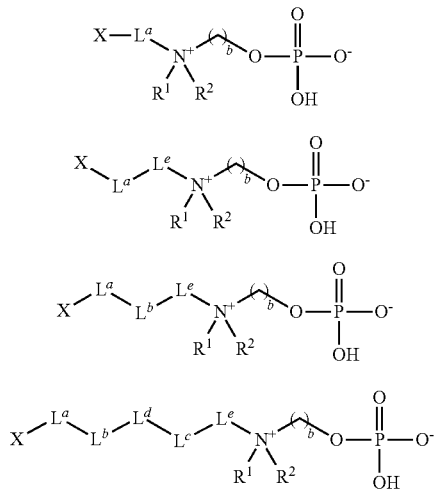

wherein
-L$^a$- represents: —(CH$_2$)$_m$— or —(CH$_2$—CH$_2$—O)$_m$—CH$_2$—;
-L$^b$- and -L$^c$- are independently of each other selected from: —O—, —NH—C(O)—, —C(O)—NH—, —O—C(O)—NH— and —SO$_2$—;
-L$^d$- represents: —(CH$_2$)$_n$— or —(CH$_2$—CH$_2$—O)$_n$—CH$_2$—;
-L$^e$- is selected from: —(CH$_2$)$_{p1}$— and —(CH$_2$)$_{p1}$—O—(CH$_2$)$_{p2}$—,
m, n, p1 and p2 are independently of each other selected from 1, 2, 3, 4, 5, 6, 7, 8, 9, 10;
and b, X, R$^1$ and R$^2$ have the meanings defined above.

Especially preferred compounds are compounds of general formulae (I), (III), (IV), (V) and (VI), wherein
R$^1$ and R$^2$ are independently of each other selected from: —CH$_3$ and —C$_2$H$_5$;
X is selected from: —SH and —NHR$^3$;
R$^3$ is selected from: —H, —CH$_3$, —C$_2$H$_5$ and —C$_3$H$_7$; and
-L$^a$- represents: —(CH$_2$)$_m$—.

A even more preferred embodiment is directed to compounds of general formula (I)

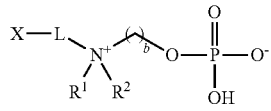

wherein b is selected from 2 and 3;
R$^1$ and R$^2$ are independently of each other selected from: —CH$_3$, —C$_2$H$_5$, —C$_3$H$_7$, —C$_4$H$_9$, —C$_5$H$_{11}$, —C$_6$H$_{13}$, or R$^1$ and R$^2$ can form together with the nitrogen atom to which they are connected a heterocycle selected from:

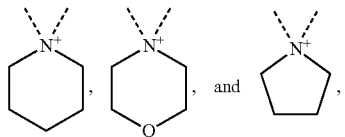

wherein one or several hydrogen atom(s) can be replaced with (a) fluorine atom(s),
X is selected from: —SH, —NHR$^3$, —C≡CH, —CH═CH$_2$, —N$_3$ and —CHO;
R$^3$ is selected from: —H, —CH$_3$, —C$_2$H$_5$, —C$_3$H$_7$;
-L- is selected from: —(CH$_2$)$_m$—, —(CH$_2$)$_m$—O—C(O)—NH—(CH$_2$)$_{p1}$—, —(CH$_2$)$_m$—O—(CH$_2$)$_{p1}$—, —(CH$_2$)$_m$—C(O)—NH—(CH$_2$)$_{p1}$—, —(CH$_2$)$_m$—NH—C(O)—(CH$_2$)$_{p1}$—,
—(CH$_2$)$_m$—C(O)—NH—(CH$_2$)$_n$—O—(CH$_2$)$_{p1}$—,
—(CH$_2$)$_m$—O—C(O)—NH—(CH$_2$)$_n$—O—(CH$_2$)$_{p1}$—,
—(CH$_2$)$_m$—C(O)—NH—(CH$_2$)$_n$—C(O)—NH—(CH$_2$)$_{p1}$—O—(CH$_2$)$_{p2}$—, and
—(CH$_2$)$_m$—O—C(O)—NH—(CH$_2$)$_n$—C(O)—NH—(CH$_2$)$_{p1}$—O—(CH$_2$)$_{p2}$—;

and m, n, p1 and p2 are independently of each other selected from 1, 2, 3, 4, 5, 6, 7, 8, 9, 10.

Preferably the compounds of general formula (I) are selected from:

1 2-[2-(2-aminoethoxy)ethyl-diethyl-ammonio]ethyl hydrogen phosphate

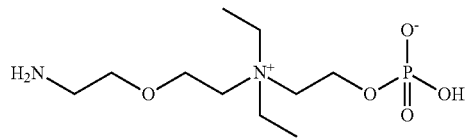 [SMILES: CC[N+](CC)(CCOCCN)CCOP(=O)([O-])O]

2  2-[4-[2-(2-aminoethoxy)ethyl]morpholin-4-ium-4-yl]ethyl hydrogen phosphate

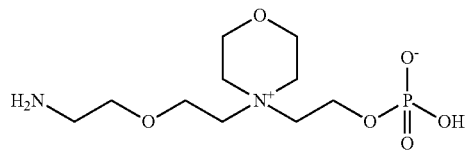 [SMILES: NCCOCC[N+]1(CCOP(=O)([O-])O)CCOCC1]

3  2-[1-[2-(2-aminoethoxy)ethyl]piperidin-1-ium-1-yl]ethyl hydrogen phosphate

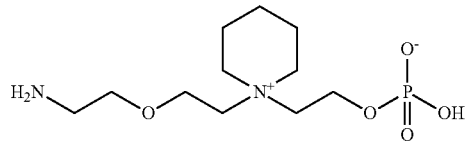 [SMILES: NCCOCC[N+]1(CCOP(=O)([O-])O)CCCCC1]

4  2-[2-(2-aminoethoxy)ethyl-dimethyl-ammonio]ethyl hydrogen phosphate

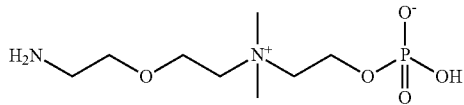 [SMILES: C[N+](C)(CCOCCN)CCOP(=O)([O-])O]

5  2-[3-aminopropyl(dimethyl)ammonio]ethyl hydrogen phosphate

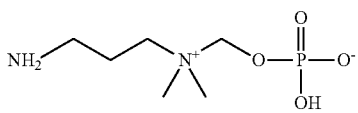

6  2-[dimethyl(4-sulfanylbutyl)ammonio]ethyl hydrogen phosphate

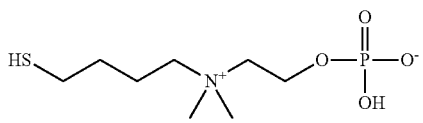

7  2-[4-azidobutyl(dimethyl)ammonio]ethyl hydrogen phosphate

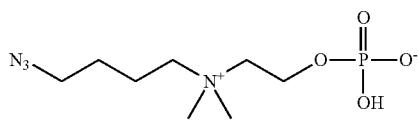 [SMILES: C[N+](C)(CCCCN=[N+]=[N-])CCOP(=O)([O-])O]

8  2-[dimethyl(pent-4-ynyl)ammonio]ethyl hydrogen phosphate

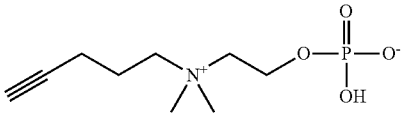

9  2-[3-(6-aminohexanoylamino)propyl-diethyl-ammonio]ethyl hydrogen phosphate

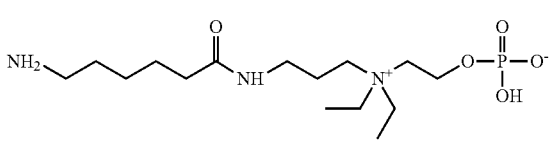 [SMILES: CC[N+](CC)(CCCNC(=O)CCCCCN)CCOP(=O)([O-])O]

10  2-[1-[2-[2-(6-aminohexanoylamino)ethoxy]ethyl]piperidin-1-ium-1-yl]ethyl hydrogen phosphate

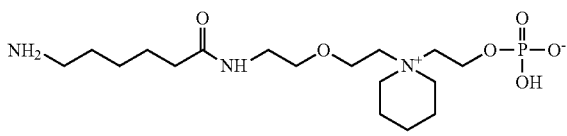 [SMILES: NCCCCCC(=O)NCCOCC[N+]1(CCOP(=O)([O-])O)CCCCC1]

11  2-[4-[2-[2-[3-(6-aminohexanoylamino)propanoylamino]ethoxy]ethyl]morpholin-4-ium-4-yl]ethyl hydrogen phosphate

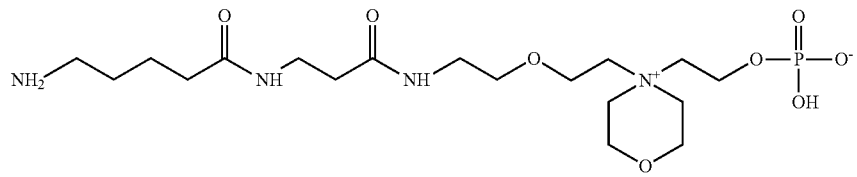 [SMILES: NCCCCC(=O)NCCC(=O)NCCOCC[N+]1(CCOP(=O)([O-])O)CCOCC1]

12  2-[1-[2-[2-[6-(6-aminohexanoylamino)hexanoylamino]ethoxy]ethyl]pyrrolidin-1-ium-1-yl]ethyl hydrogen phosphate

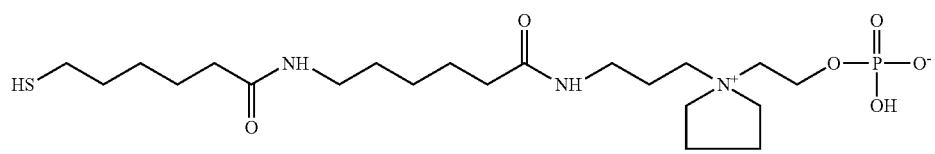 [SMILES: O=C(CCCCCS)NCCCCCC(=O)NCCC[N+]1(CCOP(=O)([O-])O)CCCC1]

13  2-[2-allyloxyethyl(dimethyl)ammonio]ethyl hydrogen phosphate

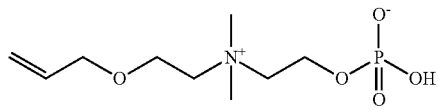 [SMILES: C=CCOCC[N+](C)(C)CCOP(=O)([O-])O]

14  2-[2-allyloxyethyl(diethyl)ammonio]ethyl hydrogen phosphate

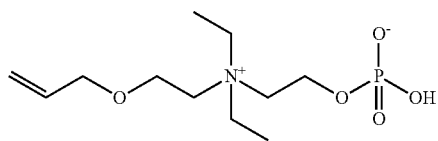 [SMILES: C=CCOCC[N+](CC)(CC)CCOP(=O)([O-])O]

15  2-[4-(2-allyloxyethyl)morpholin-4-ium-4-yl]ethyl hydrogen phosphate

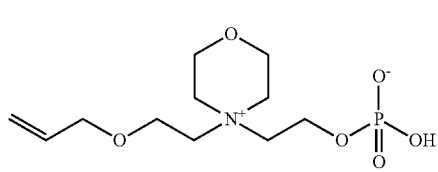 [SMILES: C=CCOCC[N+]1(CCOP(=O)([O-])O)CCOCC1]

16  2-[1-(2-allyloxyethyl)piperidin-1-ium-1-yl]ethyl hydrogen phosphate

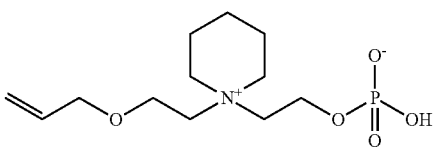 [SMILES: C=CCOCC[N+]1(CCOP(=O)([O-])O)CCCCC1]

17  2-[2-[2-(6-aminohexanoylamino)ethoxy]ethyl-dimethyl-ammonio]ethyl hydrogen phosphate

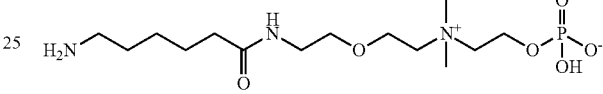

18  2-[2-[2-[3-(6-aminohexanoylamino)propanoylamino]ethoxy]ethyl-dimethyl-ammonio]ethyl hydrogen phosphate

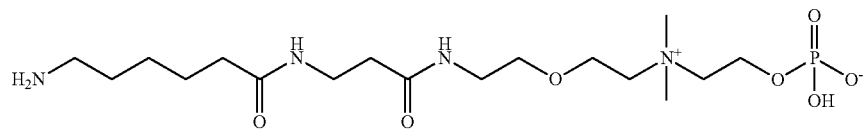 [SMILES: C[N+](C)(CCOCCNC(=O)CCNC(=O)CCCCCN)CCOP(=O)([O-])O]

19  2-[3-azidopropyl(dimethyl)ammonio]ethyl hydrogen phosphate

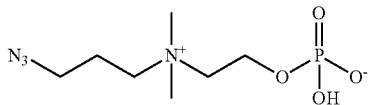 [SMILES: C[N+](C)(CCCN=[N+]=[N-])CCOP(=O)([O-])O]

20  2-[dimethyl-[2-[2-(prop-2-ynoxycarbonylamino)ethoxy]ethyl]ammonio]ethyl hydrogen phosphate

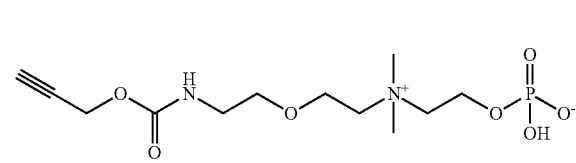 [SMILES: C#CCOC(=O)NCCOCC[N+](C)(C)CCOP(=O)([O-])O]

21  2-[2-[2-(allyloxycarbonylamino)ethoxy]ethyl-dimethyl-ammonio]ethyl hydrogen phosphate

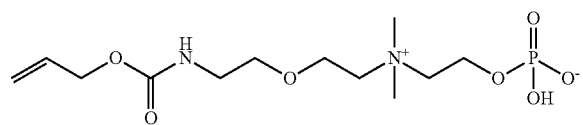 [SMILES: C=CCOC(=O)NCCOCC[N+](C)(C)CCOP(=O)([O-])O]

22  2-[2-[2-[6-(allyloxycarbonylamino)hexanoylamino]ethoxy]ethyl-dimethyl-ammonio]ethyl hydrogen phosphate

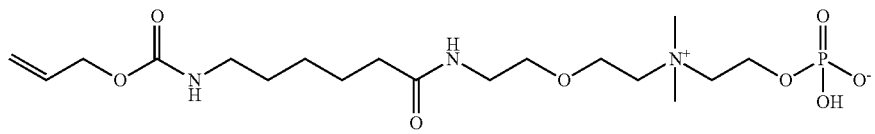 [SMILES: C=CCOC(=O)NCCCCCC(=O)NCCOCC[N+](C)(C)CCOP(=O)([O-])O]

23  2-[2-(6-aminohexanoylamino)ethyl-dimethyl-ammonio]ethyl hydrogen phosphate

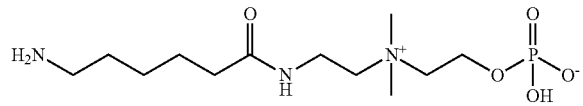 [SMILES: C[N+](C)(CCNC(=O)CCCCCN)CCOP(=O)([O-])O]

24  2-[dimethyl-[3-[6-(prop-2-ynoxycarbonylamino)hexanoylamino]propyl]ammonio]ethyl hydrogen phosphate

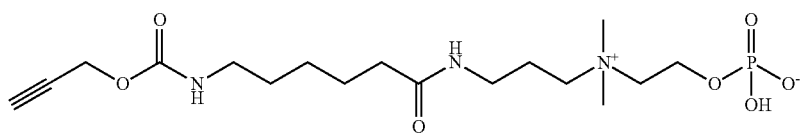 [SMILES: C#CCOC(=O)NCCCCCC(=O)NCCC[N+](C)(C)CCOP(=O)([O-])O]

25  2-[3-(6-aminohexanoylamino)propyl-dimethyl-ammonio]ethyl hydrogen phosphate

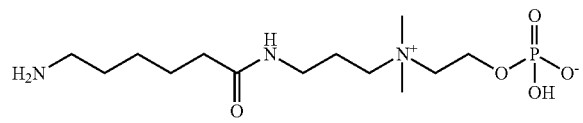 [SMILES: C[N+](C)(CCCNC(=O)CCCCCN)CCOP(=O)([O-])O]

The inventive compounds of the present invention were designed so that they can be immobilized on solid supports to provide separation materials that present increased stability, increased affinity and increased selectivity for CRP in comparison to the separation materials disclosed by the prior art. This was achieved by replacing one of the alkyl substituent of the tri-alkyl ammonium group of the phosphoryl choline with the moiety -L-X. The moiety -L-X enables the immobilization of the compounds of general formula (I) to a solid support without modifying the overall charge of the phosphoryl choline molecule and by avoiding the presence of the unstable phosphodiester bond in the construct.

Hence, the present invention further provides a separation material of general formula (II):

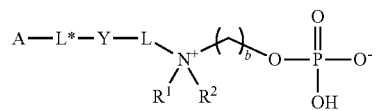

(II)

wherein
b is selected from 2 and 3;
$R^1$ and $R^2$ are independently of each other selected from: —$CH_3$, —$C_2H_5$, —$C_3H_7$, —$C_4H_9$, —$C_5H_{11}$ and —$C_6H_{13}$, or $R^1$ and $R^2$ can form together with the nitrogen atom to which they are connected a heterocycle selected from:

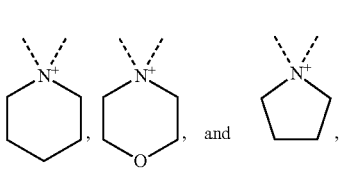

wherein one or several hydrogen atom(s) can be replaced with (a) fluorine atom(s);

Y is selected from: —CH(OH)—$CH_2$—N($R^4$)—, —CH(OH)—$CH_2$—S—, —$CH_2$—NH—, —NH—$CH_2$—, —$CH_2$—$CH_2$—S—, —S—$CH_2$—$CH_2$—,

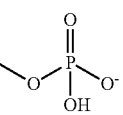 , 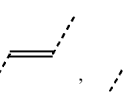 , 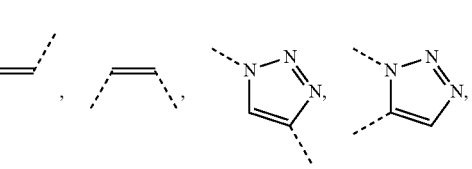

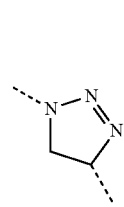 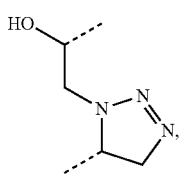

-continued

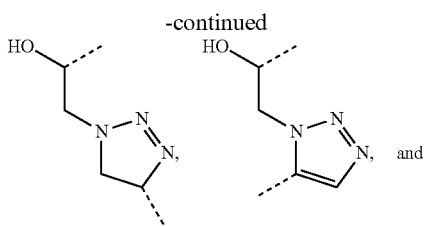

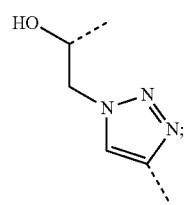

$R^4$ is selected from: —H, —$CH_3$, —$C_2H_5$, —$C_3H_7$ and —C(O)—$CH_3$;

-L- is selected from: -$L^a$-, -$L^a$-$L^e$-, -$L^a$-$L^b$-$L^e$- and -$L^a$-$L^b$-$L^d$-$L^c$-$L^e$-, wherein -$L^a$- is selected from: —$(CH_2)_m$—, —$(CH_2$—$CH_2$—O$)_m$—$CH_2$—,

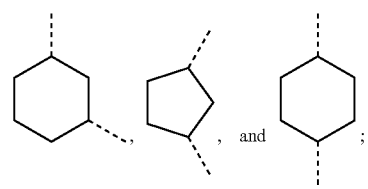

-$L^b$- and -$L^c$- are independently of each other selected from: —O—, —NH—C(O)—, —C(O)—NH—, —O—C(O)—NH— and —$SO_2$—;

-$L^d$- is selected from: —$(CH_2)_n$—, —$(CH_2$—$CH_2$—O$)_n$—$CH_2$—,

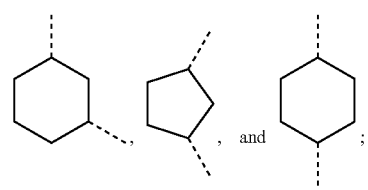

-$L^e$- is selected from: —$(CH_2)_{p1}$—, —$(CH_2)_{p1}$—O—$(CH_2)_{p2}$—,

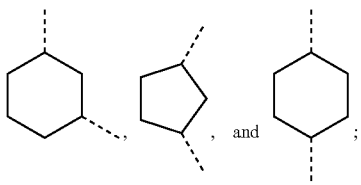

-L*- is selected from: -$L^{*a}$-, -$L^{*a}$-$L^{*e}$- and -$L^{*a}$-$L^{*b}$-$L^{*e}$-, wherein -$L^{*a}$- is selected from: —$(CH_2)_o$—, —$(CH_2$—$CH_2$—O$)_o$—$C_2H_4$—, —$(CH_2$—$CH_2$—O$)_o$—$CH_2$— and —$CH_2$—CH(OH)—$CH_2$—;

-$L^{*e}$- is selected from: —$(CH_2)_q$—, —$C_2H_4$—(O—$CH_2$—$CH_2)_q$—, and —$CH_2$—(O—$CH_2$—$CH_2)_q$—;

-$L^{*b}$- is selected from: —O—$(CH_2)_r$—O—, —S—$(CH_2)_r$—S—, —$SO_2$—, —S—, —O—, —NH—C(O), —C(O)—NH— and —S—S—; and m, n, p1, p2, o, r, q are independently of each other selected from 1, 2, 3, 4, 5, 6, 7, 8, 9, 10;

A is a solid support selected from the group consisting of: polyvinylpyrrolidone (PVP), polysulfone (PS), polyethersulfone (PES), polyarylethersulfone (PAES), polyacrylate, poly(methyl methacrylate) (PMMA), poly(glycidyl methacrylate) (PGMA), poly(hydroxy metacrylate), polystyrene (PS), polytetrafluoroethylene (PTFE), polyacrylamide, polyacrolein, acrylonitrile butadiene styrene (ABS), polyacrylonitrile (PAN), polyurethane (PU), Eupergit®, polyethylene glycol (PEG), hyperfluorocarbon, agarose, alginate, carrageenan, chitin, starch, cellulose, nitrocellulose, Sepharose®, glass, silica, kieselguhr, zirconia, alumina, iron oxide and mixture and/or derivatives of said solid supports; and protonated and deprotonated forms of this separation material.

It is clear to the skilled person that the left extremity of the fragment -L*- is connected to A, the right extremity of the fragment -L*- is connected to the left extremity of the fragment Y, the right extremity of the fragment Y is connected to the left extremity of the fragment -L-, whose right extremity is connected to

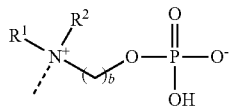

Same applies to the fragments: -$L^a$-, -$L^b$-, -$L^c$-, -$L^d$-, -$L^e$-, -$L^{*a}$-, -$L^{*b}$- and -$L^{*e}$-.

Thus, for example, if -L*- represents -$L^{*a}$-$L^{*b}$-$L^{*e}$- with -$L^{*a}$- being —$CH_2$—CH(OH)—$CH_2$—, -$L^{*b}$- being —O—, -$L^{*e}$- being —$(CH_2)_q$—, Y represents —CH(OH)—$CH_2$—N($R^4$)—, -L- represents -$L^a$-$L^b$-$L^e$- with -$L^a$- being —$(CH_2)_m$—, -$L^b$- being —O—C(O)—NH—, and -$L^e$- being —$(CH_2)_{p1}$—O—$(CH_2)_{p2}$—, then the separation material of general formula (II) is the following:

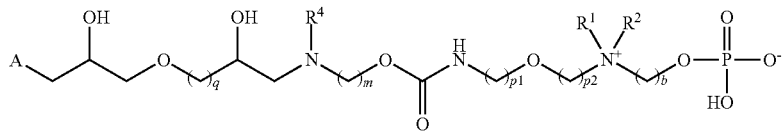

As used herein the solid support A refers to an inert solid support that in anticipation of the covalent immobilization of the inventive compounds of general formula (I), (III), (IV), (V) and (VI) is functionalized with the moiety -L*-FG, wherein FG is a reactive functional group that is suitable to react with the functional group X. Examples of FG groups include, but are not restricted to: epoxide, —CHO, —C≡CH, —CH═CH$_2$, —N$_3$, —CH(OH)—CH$_2$—N$_3$, —NH$_2$, —SH, tresyl. The functionalization of the solid support is achieved through methods well known to the person skilled in the art (*Chin. J. Chem.* 2012, 30, 2473; *Polym. Int.* 2013, 62, 991). In addition, functionalized solid supports are already commercially available: Toyopearl® AF-epoxy, Toyopearl® AF-amino, Toyopearl® AF-tresyl, TSKgel® tresyl, epoxy-activated Sepharose® 6B (GE Healthcare Life Sciences), CNBr-activated Sepharose® 4 fast flow (GE Healthcare Life Sciences), ECH Sepharose® 4B (GE Healthcare Life Sciences), NHS-activated Sepharose® 4 fast flow (GE Healthcare Life Sciences), terminal vinylsulfone activated Sepharose® 4 fast flow (Affiland), aldehyde Separopore® (Agarose) 4B, ECH Separopore® (Agarose) 4B (Separopore).

The solid support can be subjected to cross-linking or other treatments to increase physical or chemical stability, and can be formed into various shapes, including but not limited to fibers, sheets, rods, beads, and membranes.

Preferably, the solid support A is selected from polysulfone (PS), polyethersulfone (PES), polyarylethersulfone (PAES), mixtures and/or derivatives thereof.

PS, PES and PAES based solid supports can be modified so that to present on their surface the moiety -L*-FG, wherein FG is a reactive functional group that is suitable to react with the functional group X (*Chin. J. Chem.* 2012, 30, 2473; *Polym. Int.* 2013, 62, 991). Such modification results in the increase of the antifouling property, biocompatibility and other specific functions.

Preferred separation materials of the current invention are separation materials of general formula (II):

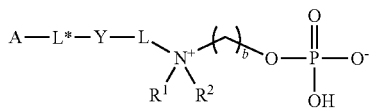

(II)

and protonated and deprotonated forms thereof
wherein
b is selected from 2 and 3;
$R^1$ and $R^2$ are independently of each other selected from: —CH$_3$, —C$_2$H$_5$, or $R^1$ and $R^2$ can form together with the nitrogen atom to which they are connected a heterocycle selected from:

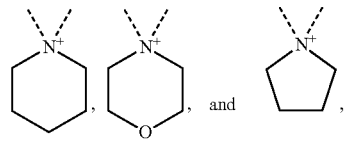

wherein one or several hydrogen atom(s) can be replaced with (a) fluorine atom(s),
Y is selected from: —CH(OH)—CH$_2$—N(R$^4$)—, —CH(OH)CH$_2$—S—, —CH$_2$—NH—, —NH—CH$_2$—, —CH$_2$—CH$_2$—S—, —S—CH$_2$—CH$_2$—,

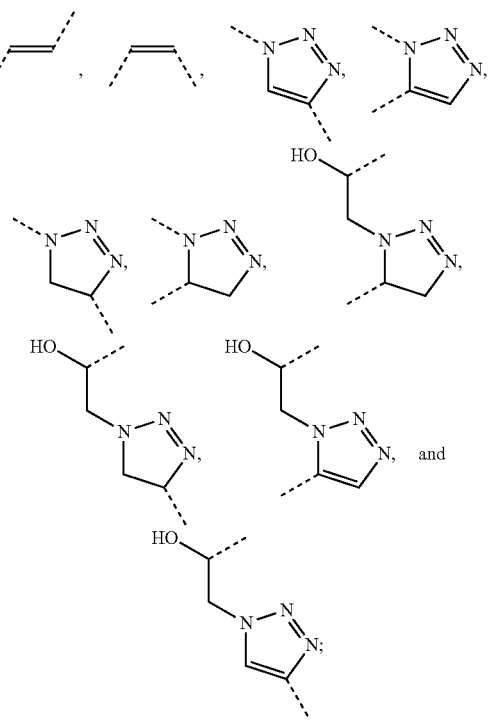

$R^4$ is selected from: —H, —CH$_3$, —C$_2$H$_5$, —C$_3$H$_7$, —C(O)—CH$_3$;
-L- is selected from: -L$^a$-, -L$^a$-L$^e$-, -L$^a$-L$^b$-L$^e$- and -L$^a$-L$^b$-L$^d$-L$^c$-L$^e$-, wherein
-L$^a$- represents: —(CH$_2$)$_m$— or —(CH$_2$—CH$_2$—O)$_m$—CH$_2$—;
-L$^b$- and -L$^c$- are independently of each other selected from: —O—, —NH—C(O)—, —C(O)—NH—, —O—C(O)—NH— and —SO$_2$—;
-L$^d$- is selected from: —(CH$_2$)$_n$— and —(CH$_2$—CH$_2$—O)$_n$—CH$_2$—,
-L$^e$- is selected from: —(CH$_2$)$_{p1}$— and —(CH$_2$)$_{p1}$—O—(CH$_2$)$_{p2}$—;
-L*- is selected from: -L*$^a$-, -L*$^a$-L*$^e$- and -L*$^a$-L*$^b$-L*$^e$-, wherein -L*$^a$- is selected from: —(CH$_2$)$_o$—, —(CH$_2$—CH$_2$—O)$_o$—C$_2$H$_4$—, —(CH$_2$—CH$_2$—O)$_o$—CH$_2$— and —CH$_2$—CH(OH)—CH$_2$—;

-L*$^e$- is selected from: —(CH$_2$)$_q$—, —C$_2$H$_4$—(O—CH$_2$—CH$_2$)$_q$—, and —CH$_2$—(O—CH$_2$—CH$_2$)$_q$—;

-L*$^b$- is selected from: —O—(CH$_2$)$_r$—O—, —S—(CH$_2$)$_r$—S—, —SO$_2$—, —S—, —O—, —NH—C(O)—, —C(O)—NH— and —S—S—;

m, n, p1, p2, o, r, q are independently of each other selected from 1, 2, 3, 4, 5, 6, 7, 8, 9, 10;

and A has the meaning defined above, and more preferably A is selected from polysulfone (PS), polyethersulfone (PES), polyarylethersulfone (PAES), mixtures and/or derivatives thereof.

A preferred embodiment according to the present invention is directed to separation materials of general formula (II), wherein Y is selected from: —CH(OH)—CH$_2$—N(R$^4$)—, —CH(OH)—CH$_2$—S—, —CH$_2$—NH—, —NH—CH$_2$—, —CH$_2$—CH$_2$—S—, —S—CH$_2$—CH$_2$—,

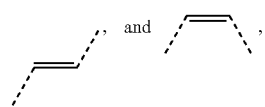

and more preferably selected from: —CH(OH)—CH$_2$—N(R$^4$)—, and —CH(OH)—CH$_2$—S—.

Also preferred are separation materials of general formula (II), wherein Y represents:

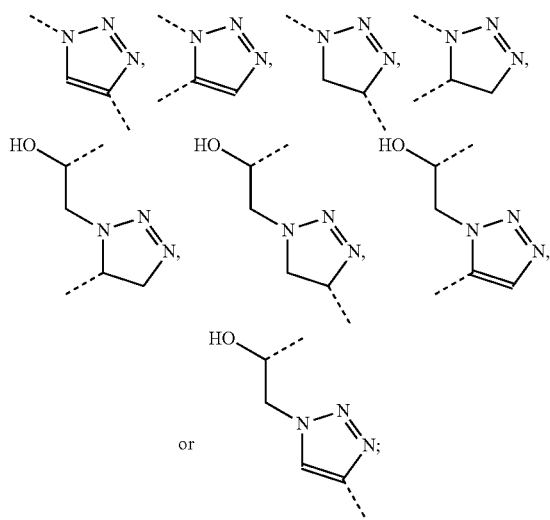

Preferred compounds of the current invention are compounds of the following general formula (VII), (VIII), (IX) and (X)

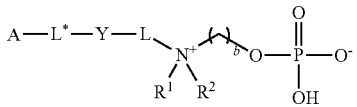

VII

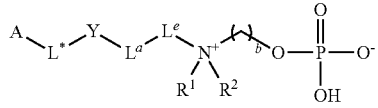

VIII

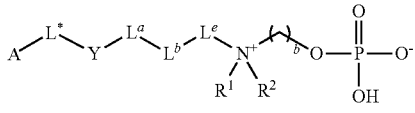

IX

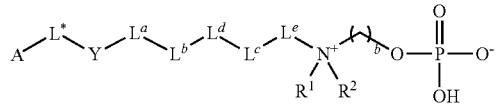

X wherein
-L$^a$- is selected from: —(CH$_2$)$_m$— and —(CH$_2$—CH$_2$—O)$_m$—CH$_2$—;

-L$^b$- and -L$^c$- are independently of each other selected from: —O—, —NH—C(O)—, —C(O)—NH—, —O—C(O)—NH— and —SO$_2$—;

-L$^d$- is selected from: —(CH$_2$)$_n$— and —(CH$_2$—CH$_2$—O)$_n$—CH$_2$—;

-L$^e$- is selected from: —(CH$_2$)$_{p1}$— and —(CH$_2$)$_{p1}$—O—(CH$_2$)$_{p2}$—;

m, n, p1, p2, o, r, q are independently of each other selected from: 1, 2, 3, 4, 5, 6, 7, 8, 9, 10; and b, A, L*, Y, R$^1$ and R$^2$ have the meanings defined above.

Especially preferred separation materials are separation materials of general formulae (II), (VII), (VIII), (IX) and (X), wherein
-L*- is selected from: -L*$^a$-, and -L*$^a$-L*$^b$-L*$^e$-; and
-L*$^a$- is selected from: —(CH$_2$)$_o$— and —CH$_2$—CH(OH)—CH$_2$—;
-L*$^e$- represents —(CH$_2$)$_q$—;
-L*$^b$- is selected from: —O—(CH$_2$)$_r$—O—, —S—(CH$_2$)$_r$—S—, —S— and —O—; and o, q and r are independently of each other selected from 1, 2, 3, 4, 5, 6, 7, 8, 9, 10.

In the general formulae (II), (VII), (VIII), (IX) and (X), L* preferably represents -L*$^a$-L*$^b$-L*$^e$- and A is preferably selected from: polysulfone (PS), polyethersulfone (PES), polyarylethersulfone (PAES), mixtures and/or derivatives thereof.

Another preferred embodiment of the present invention is directed to separation materials of general formulae (II), (VII), (VIII), (IX) and (X), wherein
R$^1$ and R$^2$ are independently of each other selected from: —CH$_3$ and —C$_2$H$_5$;
Y is selected from: —CH(OH)—CH$_2$—N(R$^4$)—, —CH(OH)—CH$_2$-S—, —CH(OH)—CH$_2$—O—, —CH$_2$—NH—, —S—CH$_2$—CH$_2$— and —CH$_2$—CH$_2$—S—;
R$^4$ is selected from: —H, —CH$_3$, —C$_2$H$_5$, —C$_3$H$_7$ and —C(O)—CH$_3$, and
-L$^a$- represents —(CH$_2$)$_m$—.

A even more preferred embodiment is directed to a separation material of general formula (II)

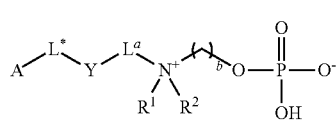

(II)

wherein
$R^1$ and $R^2$ are independently of each other selected from: —$CH_3$, —$C_2H_5$, —$C_3H_7$, —$C_4H_9$, —$C_5H_{11}$ and —$C_6H_{13}$, or $R^1$ and $R^2$ can form together with the nitrogen atom to which they are connected a heterocycle selected from:

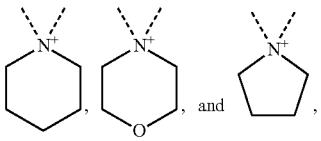

wherein one or several hydrogen atom(s) can be replaced with (a) fluorine atom(s), Y is selected from: —CH(OH)—$CH_2$—N($R^4$)—, —CH(OH)—$CH_2$—S—, —$CH_2$—NH—, —NH—$CH_2$—, —S—$CH_2$—$CH_2$— and —$CH_2$—$CH_2$—S—,

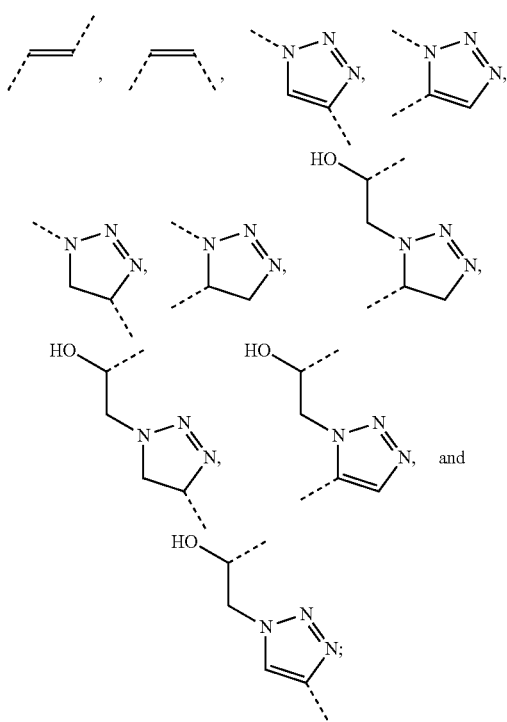

$R^4$ is selected from: —H, —$CH_3$, —$C_2H_5$, —$C_3H_7$ and —C(O)—$CH_3$;

-L- is selected from: —$(CH_2)_m$—, —$(CH_2)_m$—O—C(O)—NH—$(CH_2)_{p1}$—, —$(CH_2)_m$—O$(CH_2)_{p1}$—, —$(CH_2)_m$—C(O)—NH—$(CH_2)_{p1}$—, —$(CH_2)_m$—NH—C(O)$(CH_2)_{p1}$—, —$(CH_2)_m$—C(O)—NH—$(CH_2)_n$—O—$(CH_2)_{p1}$—,
—$(CH_2)_m$—O—C(O)—NH—$(CH_2)_n$—O—$(CH_2)_{p1}$—,
—$(CH_2)_m$—C(O)—NH$(CH_2)_n$—C(O)—NH—$(CH_2)_{p1}$—O—$(CH_2)_{p2}$— and
—$(CH_2)_m$—O—C(O)—NH—$(CH_2)_n$—C(O)—NH—$(CH_2)_{p1}$—O—$(CH_2)_{p2}$—;

m, n, p1 and p2 are independently of each other selected from 1, 2, 3, 4, 5, 6, 7, 8, 9, 10 and b, A and L* have the meanings defined above, and more preferably A is selected from: polysulfone (PS), polyethersulfone (PES), polyarylethersulfone (PAES), mixtures and/or derivatives thereof and protonated and deprotonated forms of said separation material.

Another preferred embodiment relates to a separation material of general formula (II)

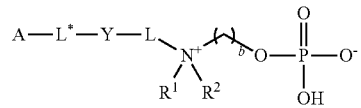

wherein b is selected from 2 and 3;
$R^1$ and $R^2$ are independently of each other selected from: —$CH_3$, —$C_2H_5$, —$C_3H_7$, —$C_4H_9$, —$C_5H_{11}$ and —$C_6H_{13}$, or $R^1$ and $R^2$ can form together with the nitrogen atom to which they are connected a heterocycle selected from:

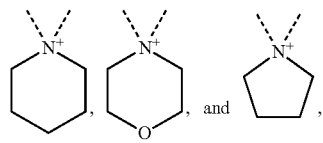

wherein one or more hydrogen atom(s) can be replaced with (a) fluorine atom(s);

Y is selected from: —CH(OH)—$CH_2$—N($R^4$)—, —CH(OH)—$CH_2$—S—, —S—$CH_2$—$CH_2$— and —$CH_2$—$CH_2$—S—;

$R^4$ is selected from: —H, —$CH_3$, —$C_2H_5$, —$C_3H_7$ and —C(O)—$CH_3$;

-L- is selected from: —$(CH_2)_m$—, —$(CH_2)_m$—O—C(O)—NH—$(CH_2)_{p1}$—, —$(CH_2)_m$—O—$(CH_2)_{p1}$—, —$(CH_2)_m$—C(O)—NH—$(CH_2)_{p1}$—, —$(CH_2)_m$—NH—C(O)—$(CH_2)_{p1}$—, —$(CH_2)_m$—C(O)—NH—$(CH_2)_n$—O—$(CH_2)_{p1}$—,
—$(CH_2)_m$—O—C(O)—NH—$(CH_2)_n$—O—$(CH_2)_{p1}$—,
—$(CH_2)_m$—C(O)—NH—$(CH_2)_n$—C(O)—NH—$(CH_2)_{p1}$—O—$(CH_2)_{p2}$— and
—$(CH_2)_m$—O—C(O)—NH—$(CH_2)_n$—C(O)—NH—$(CH_2)_{p1}$—O—$(CH_2)_{p2}$—; and m, n, p1 and p2 are independently of each other selected from 1, 2, 3, 4, 5, 6, 7, 8, 9, 10;

-L*- is selected from: —$(CH_2)_o$—, —$(CH_2$—$CH_2$—O$)_o$—$C_2H_4$—, —$(CH_2$—$CH_2$—O$)_o$—$CH_2$—C(O)—NH—$(CH_2)_q$—, —$(CH_2)_o$—$SO_2$—$(CH_2)_q$—, —$CH_2$—CH(OH)—$CH_2$—O—$CH_2$—, —$CH_2$—CH(OH)—$CH_2$—O—$(CH_2)_r$—O—$CH_2$—, and —$(CH_2$—$CH_2$—O$)_o$—$C_2H_4$—O—$CH_2$—;

o, r and q are independently of each other selected from 1, 2, 3, 4, 5, 6, 7, 8, 9, 10; and A has the meaning defined above and more preferably is selected from: polysulfone (PS), polyethersulfone (PES), polyarylethersulfone (PAES), mixtures and/or derivatives thereof.

Another preferred embodiment relates to separation materials of general formula (II)

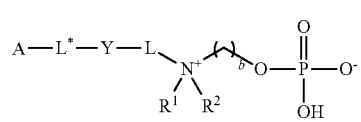

and protonated and deprotonated forms thereof
wherein b is selected from 2 and 3;
$R^1$ and $R^2$ are independently of each other selected from: —$CH_3$, —$C_2H_5$, —$C_3H_7$, —$C_4H_9$, —$C_5H_{11}$ and —$C_6H_{13}$, or $R^1$ and $R^2$ can form together with the nitrogen atom to which they are connected a heterocycle selected from:

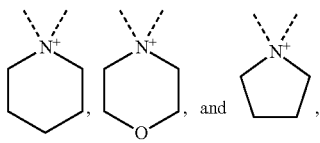

wherein one or several hydrogen atom(s) can be replaced with (a) fluorine atom(s),
Y is selected from:

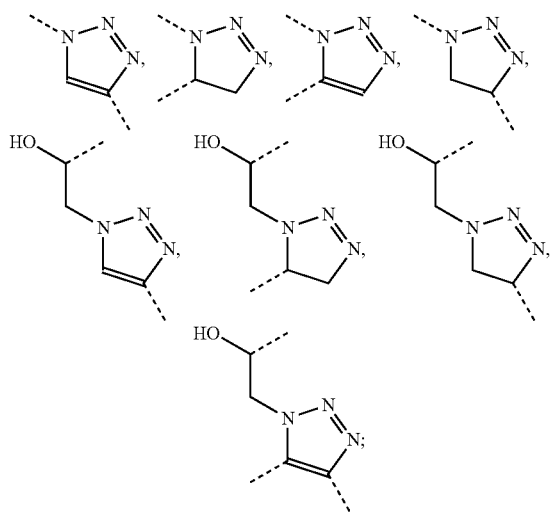

-L- is selected from: —$(CH_2)_m$—, —$(CH_2)_m$—O—C(O)—NH—$(CH_2)_{p1}$—, —$(CH_2)_m$—O—$(CH_2)_{p1}$—, —$(CH_2)_m$—C(O)—NH—$(CH_2)_{p1}$—, —$(CH_2)_m$—NH—C(O)—$(CH_2)_{p1}$—, —$(CH_2)_m$—C(O)—NH—$(CH_2)_m$—O—$(CH_2)_{p1}$—,
—$(CH_2)_m$—O—C(O)—NH—$(CH_2)_n$—O—$(CH_2)_{p1}$—,
—$(CH_2)_m$—C(O)—NH—$(CH_2)_n$—C(O)—NH—$(CH_2)_{p1}$—O—$(CH_2)_{p2}$— and
—$(CH_2)_m$—O—C(O)—NH—$(CH_2)_n$—C(O)—NH—$(CH_2)_{p1}$—O—$(CH_2)_{p2}$—; and m, n, p1 and p2 are independently of each other selected from 1, 2, 3, 4, 5, 6, 7, 8, 9, 10;
-L*- is selected from: —$(CH_2)_o$—, —$(CH_2—CH_2—O)_o$—$C_2H_4$—,
—$(CH_2—CH_2—O)_o CH_2$—C(O)—NH—$(CH_2)_q$—,
—$(CH_2)_o$—$SO_2$—$(CH_2)_q$—, —$CH_2$—CH(OH)—$CH_2$—O—$CH_2$—, —$CH_2$—CH(OH)—$CH_2$—O—$(CH_2)_r$—O—$CH_2$—, and —$(OH_2—OH_2—O)_o$—$C_2H_4$—O—$OH_2$—;
o, r, and q are independently of each other selected from 1, 2, 3, 4, 5, 6, 7, 8, 9, 10; and A has the meaning defined above and more preferably is selected from polysulfone (PS), polyethersulfone (PES), polyarylethersulfone (PAES), mixtures and/or derivatives thereof.

Indications:

Surprisingly it was found that the above-mentioned compounds of general formula (I), (III), (IV), (V) and (VI), as well as the separation materials of general formula (II), (VII), (VIII), (IX) and (X) are binding with high affinity and high selectivity CRP and anti-phosphoryl choline antibodies. Therefore, the inventive compounds and separation materials are useful for removal of CRP and anti-phosphoryl choline antibodies from biological fluids.

An embodiment of the present invention is directed to a method of extracorporeal removal of CRP from a biological fluid of a patient for prophylaxis and/or treatment of immune dysfunctions and cardiovascular diseases comprising the steps:
a) providing a separation material of general formula (II), (VII), (VIII), (IX) or (X); and
b) contacting the biological fluid of the patient with the separation material.

For this purpose, the separation material of general formula (II), (VII), (VIII), (IX) and (X) is loaded into a column, said column being useful for extracorporeal removal of CRP from a biological fluid of a patient for prophylaxis and/or treatment of immune dysfunctions and cardiovascular diseases.

As used herein the term biological fluid encompasses blood, blood plasma, peritoneal fluid and lymphatic fluid.

The dimensions of the column are not critical, and they have to be chosen so that they are adapted to the flow rate of the biological fluid removed from the patient, which is highly associated to the body weight of the patient. The column comprising the separation material of the present invention must be sterilized, for example with a sterilant gas such as ethylene oxide, and either used immediately or sealed and stored for later use. Prior to use, the column must be washed with normal saline followed by a wash with normal saline containing any other suitable preparatory ingredients. The column may be of a conventional cartridge design, fluidized bed, expandable bed or a monolith. The preparation of such columns is well known to the skilled person. For example, the preparation of a column of a conventional cartridge design can be performed as described in the patent application EP 0237659 A1.

Regeneration of the column is also possible. For regeneration purposes a 0.9% saline solution could, for instance, be used for flushing the column. Thereafter the pH value is lowered by the use of a glycine/HCl buffer (pH 2.8) in order to break the connection between the CRP and the separation material, followed by a washing step with PBS (Phosphate Buffered Saline) at a pH value of 7.4 and a final washing step with 0.9% saline solution.

Optionally, the column comprising the separation material of the present invention contains additional separation materials suitable for removal of other substances of interest from a biological fluid of a patient. The other substances are preferable proteins. Examples for other substances are interleukin-6, interleukin-1, TNFα, serum amyloid P-component (SAP), PTX3, fibrinogen, antibodies (such as IgG, IgE), anti-phospholipid antibodies and components of the complement system such as C1q, C3a or C5a.

The column of the present invention can be incorporated into a device to provide a device suitable for extracorporeal removal of CRP from a biological fluid of a patient for prophylaxis and/or treatment of immune dysfunctions and cardiovascular diseases.

Thus, the device according to the present invention comprises:
a) a column comprising a separation material of general formula (II), (VII), (VIII), (IX) and (X); and
b) an apparatus for bringing ex vivo the column comprising the separation material in contact with a biological fluid of a patient, thereby decreasing the CRP level in said biological fluid and for returning the biological fluid to the patient.

Due to the high affinity and selectivity of the compounds of general formula (I), the separation material of general formula (II), (VII), (VIII), (IX) and (X), the column comprising the separation material of general formula (II), (VII), (VIII), (IX) or (X), and the device comprising the column, which comprises the separation material of general formula (II), (VII), (VIII), (IX) or (X) are particularly useful in the extracorporeal removal of CRP from a biological fluid of a patient for prophylaxis and/or treatment of immune dysfunctions and cardiovascular diseases.

Preferably, the biological fluid is selected from: blood, blood plasma, peritoneal fluid and lymphatic fluid.

The term "cardiovascular diseases" as used herein includes, but it is not limited to infarction, stroke, diabetes, end-stage renal disease, renal insufficiency, renal insufficiency due to hypertension, endothelial lesions, endothelial destruction, arteriosclerosis, thrombosis, atherosclerosis, stenosis, restenosis, atherosclerotic or thrombotic diseases, blood flow insufficiency, ischemic events, pulmonary embolism, stable and unstable angina pectoris, coronary arterial diseases, myocardial infarction, as well as pathologic results of arteriosclerotic or thrombotic diseases.

The term "immune dysfunctions" as used herein includes, but it is not limited to immune diseases, autoimmune diseases, rejection reactions in transplantations, allo-transplant rejection, xeno-transplant rejection, graft-versus-host rejection, host-versus-graft rejection, diabetes mellitus, rheumatism, rheumatoid arthritis, psoriatic arthritis, ankylosing spondilitis, multiple sclerosis, myasthenia gravis, psoriasis vulgaris, Graves' disease, Goodpasture syndrome, idiopathic thrombocytopenia purpura (ITP), aplastic anemia, inflammatory bowel disease (IBD), Crohn's disease (also known as Crohn syndrome), colitis ulcerosa, dilatative cardiomyopathy (DCM), autoimmune thyroiditis, Hashimoto's thyroiditis, hormone replacement therapy (HRT), osteoarthritis and gout.

Chemical Synthesis

A. Synthesis of Compounds of General Formula (I)

A.1 The inventive compounds of general formula I, wherein X represents —NHR$^3$, R$^3$ is selected from: —H, —CH$_3$, —C$_2$H$_5$, —C$_3$H$_7$ and -L- represents -L$^a$-, -L$^a$-O-L$^e$-, -L$^a$-L$^e$- (i.e. compounds of general formula 6), or X represents —C≡CH or —CH=CH$_2$ and -L- represents -L$^a$-O—C(O)—NH-L$^e$- or -L$^a$-O—C(O)—NH-L$^d$-O-L$^e$- (i.e. compounds of general formula 5, wherein PG$^1$ represents allyloxy carbonyl or propargyloxy carbonyl and R$^3$ represents —H) can be assembled starting from commercially available amino alcohols of general formula NHR$^3$L$^1$-OH (1), wherein L$^1$ represents -L$^a$-, -L$^a$-O-L$^e$-, -L$^a$-L$^e$-, -L$^e$-, -L$^d$-O-L$^e$-, or -L$^d$-L$^e$- according to Scheme 1.

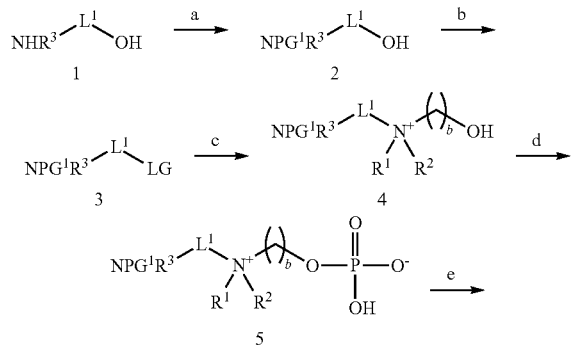

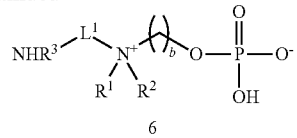

Scheme 1: Synthesis of compounds of general formula 5 and 6: a. protection amino group; b. conversion hydroxyl group to a leaving group LG; c. quaternization; d. phosphorylation; e. deprotection.

The synthesis involves protection of the terminal amino group of the amino alcohol 1 with a protecting group PG$^1$, followed by the conversion of the terminal hydroxyl group to a leaving group LG to provide intermediate 3. Suitable amino protecting group PG$^1$ are well known to the skilled person and include carbamates, phthaloyl group and substituted phthaloyl groups. Examples of carbamates include, but are not restricted to: benzyloxycarbonyl (Cbz or Z), 4-nitro-benzyloxycarbonyl, 4-chloro-benzyloxycarbonyl, 4-methoxy-benzyloxycarbonyl, 4-methyl-benzyloxycarbonyl, 4-azido-benzyloxycarbonyl, 9-fluorenylmethoxy carbonyl (Fmoc), allyloxy carbonyl (Aloc), propargyloxy carbonyl, tert-butyloxy carbonyl (Boc). Phtaloyl and substituted phtaloyl protecting groups are particularly useful for protection of primary amines (R$^3$ represents H). Example of substituted phtaloyl groups include, but are not restricted to 4-nitro-phtaloyl, 3-nitro-phtaloyl and tetrachlorophtaloyl. Preferably, protecting group PG$^1$ is selected from allyloxy carbonyl, propargyloxy carbonyl, benzyloxycarbonyl and phtaloyl. Leaving group LG installed at step b can be selected from the group comprising chloride, bromide, iodide, tosylate, benzensulfonate, p-nitro-benzenesulfonate, mesylate or triflate group. Preferably, the leaving group LG is an ester of a sulfonic acid (i.e. a sulfonate), and more preferably LG is a mesylate group. The conversion of the alcohol functionality to a group LG can be accomplished for example by treatment of alcohol 2 with MsCl or TsCl in presence of triethylamine, using dichoromethane as solvent at 0° C. Intermediate 3 is further reacted with an amino alcohol of general formula NHR$^1$R$^2$—(CH$_2$)$_b$—OH, such as dimethylethanolamine, dimethylpropanolamine, N,N-diethylethanolamine, N-(2-hydroxyethyl)morpholine, or N-(2-hydroxyethyl)piperidine to provide amino alcohol 4 via a quaternization reaction. Subsequent treatment of alcohol 4 with POCl$_3$ and triethylamine in acetonitrile at 0° C. results in the introduction of the phosphate group on the molecule. Deprotection of the terminal amino group furnishes the target compounds of general formula 6 according to the present invention that are ready to be immobilized to a solid support via the terminal amino group. If the protecting group PG$^1$ is allyloxy carbonyl or propargyloxy carbonyl and R$^3$ represents —H, then the deprotection step is optional as the compounds of general formula 5 can be directly immobilized to the solid support via the terminal alkene (thiol-ene chemistry, click chemistry, methathesis) or alkyne group (click chemistry).

A variety of commercially available amino alcohols of general formula NHR$^3$-L$^1$-OH (1) can function as a starting material for the synthetic pathway described in Scheme 1. Such commercially available amino alcohols include, but are not restricted to 2-aminoethanol, 3-amino propan-1-ol, 4-amino butan-1-ol, 5-amino pentan-1-ol, 6-amino hexan-1-ol, 2-(2-aminoethoxy)ethanol, 2-[2-(2-aminoethoxy) ethoxy]ethanol, 2-(3-aminopropoxy)ethanol. 3-(3-aminopropoxy)propan-1-ol, 4-(3-aminopropoxy)butan-1-ol, 2-(methylamino)ethanol, 3-(methylamino)propan-1-ol, 4-(methylamino)butan-1-ol, 5-(methylamino)hexan-1-ol, 6-(methylamino)hexan-1-ol, 7-(methylamino)heptan-1-ol, 2-[2-(methylamino)ethoxy]ethanol, 2-[2-[2-(methylamino)ethoxy]ethoxy]ethanol, 2-[3-(methylamino)propoxy]ethanol, 3-[3-(methylamino)propoxy]ethanol, 3-[3-(methylamino)propoxy]propan-1-ol, 4-[3-(methylamino)propoxy]butan-1-ol.

The skilled person will appreciate that by applying steps b, c and d of the synthetic procedure described in Scheme 1 and if necessary an appropriate deprotection step to an alcohol of general formula $PG^2S\text{-}L^1\text{-}OH$, $HC\equiv C\text{-}L^1\text{-}OH$, $CH_2=CH\text{-}L^1\text{-}OH$, $N_3\text{-}L^1\text{-}OH$ or $PG^3=C\text{-}L^1\text{-}OH$, wherein $PG^2$ is a sulfhydryl protecting group (e.g. benzyl) and $PG^3$ is an aldehyde protecting group (e.g. dithiane or acetal) analogues 6a, 6b, 6c, 6d and 6e will be accessed.

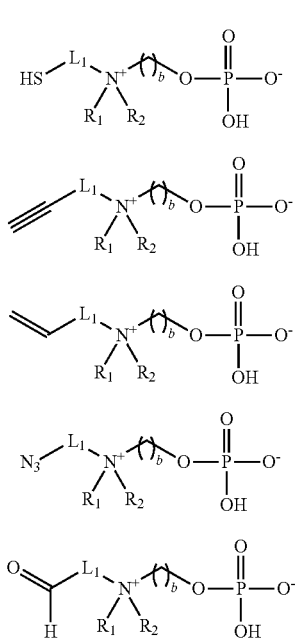

In this case propargylic alcohol, 3-azido propan-1-ol, 2-azidoethanol, 4-azidobutan-1-ol, 2-(2-azidoethoxy)ethanol, 2-[2-(2-azidoethoxy)ethoxy]ethanol, 2-[2-[2-(2-azidoethoxy)ethoxy]ethoxy]ethanol, 2-(2-azidoethylsulfonyl)ethanol, but-3-yn-1-ol, pent-4-yn-1-ol, 2-prop-2-ynoxyethanol, 2-(2-prop-2-ynoxyethoxy)ethanol, 2-[2-(2-prop-2-ynoxyethoxy)ethoxy]ethanol can be used as starting materials.

A.2 The inventive compounds of general formula I, wherein X represents —$NHR^3$, $R^3$ is selected from: —H, —$CH_3$, —$C_2H_5$, —$C_3H_7$ and -L- represents -$L^a$-C(O)—NH-$L^e$- (i.e. compounds of general formula 7 and 19) or X represents —C≡CH or —CH=$CH_2$ and -L- represents -$L^a$-O—C(O)—NH-$L^d$-C(O)—NH-$L^e$- (i.e. compounds of general formula 8 and 18, wherein $PG^1$ represents allyloxy carbonyl or propargyloxy carbonyl $R^3$ represents —H) can be assembled starting from amino acids 9 of general formula $NHR^3\text{-}L^2\text{-}CO_2H$, wherein -$L^2$- represents -$L^a$- or -$L^d$-, amino alcohols 10 of general formula $NH_2\text{-}L^1\text{-}OH$ (1), wherein $L^1$ represents -$L^e$- or diamines 11 of general formula $NH_2\text{-}L^3\text{-}NR^1R^2$, wherein $L^3$ represents -$L^e$- according to Scheme 2.

The synthesis commences with the protection of the amino group on amino acid 9 with a protecting group $PG^1$, wherein $PG^1$ has the meaning defined at the paragraph A.1 to give carboxylic acid 12. Coupling of the carboxylic acid 12 with the amino alcohol 10 furnishes primary alcohol 13 on which the hydroxyl group is further converted to leaving group LG, wherein leaving group LG has the defined at the paragraph A.1 to provide intermediate 14. Treatment of intermediate 14 with amino alcohol 10 of general formula $NHR^1R^2$—$(CH_2)_b$—OH (e.g. dimethylethanolamine, dimethylpropanolamine, N,N-diethylethanolamine, N-(2-hydroxyethyl)morpholine, or N-(2-hydroxyethyl)piperidine) results in the formation of alcohol 15 that is subjected to quaternization reaction, followed by deprotection involving cleavage of the protecting group $PG^1$ to give the target compound 7. As previously, precursor 8 with $PG^1$ being allyloxy carbonyl or propargyloxy carbonyl can be directly immobilized to a solid support.

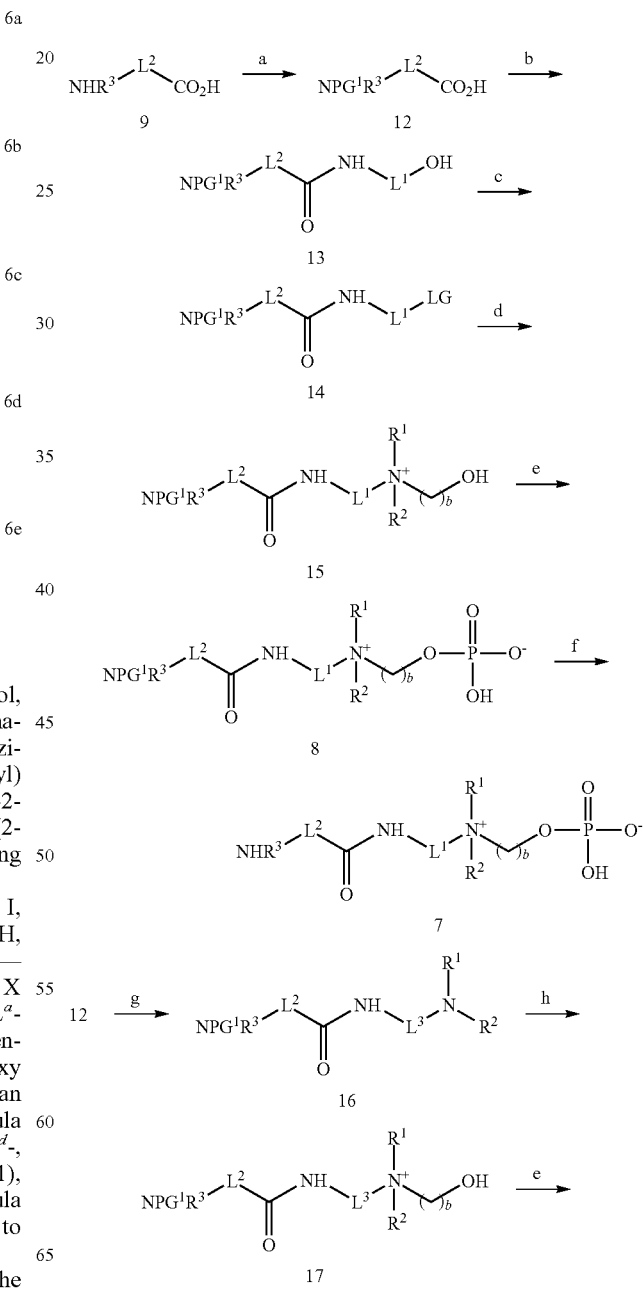

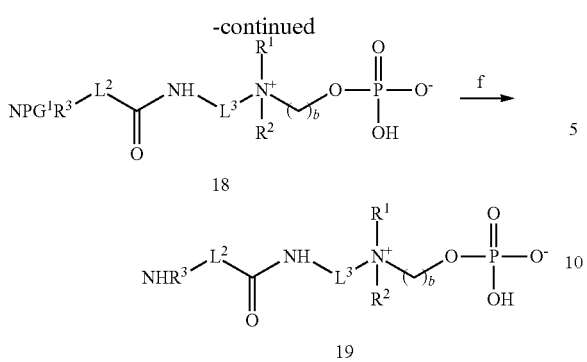

Scheme 2: Synthesis of compounds of general formula 7, 8, 18 and 19: a. protection amino group; b. 10, coupling; c. conversion hydroxy group to a leaving group LG; d. quaternization; e. phosphorylation; f. deprotection; g. 11, coupling; h. quaternization.

Alternatively, carboxylic alcohol 12 can be coupled with diamine 11 to provide amide 16 that is subsequently subjected to quaternization reaction by treatment with a 2-hydroxyethyl or 3-hydroxypropyl derivative. Suitable 2-hydroxyethyl and 3-hydroxypropyl derivatives include 2-bromo- and 2-iodo-ethanol and 3-bromo and 3-iodo propanol. The quaternization reaction is preferably performed in acetonitrile, at room temperature. Finally, phosphorylation reaction, followed by deprotection reaction applied to alcohol 18 furnishes target compound 19.

Amino acids 9 of general formula $NHR^3-L^2-CO_2H$ include, but are not restricted to 7-aminoheptanoic acid, 6-aminohexanoic acid, 5-aminopentanoic acid, 4-aminobutanoic acid, 3-aminopropanoic acid, 2-amino acetic acid, 2-[2-(2-aminoethoxy)ethoxy]acetic acid, 2-[2-[2-(2-aminoethoxy)ethoxy]ethoxy]acetic acid, 2-(2-aminoethoxy)acetic acid, 2-(3-aminopropoxy)acetic acid, 3-(3-aminopropoxy)propanoic acid, 4-(3-aminopropoxy)butanoic acid, 2-(methylamino)acetic acid, 3-(methylamino)propanoic acid, 4-(methylamino)butanoic acid, 5-(methylamino)pentanoic acid, 6-(methylamino)hexanoic acid, 7-(methylamino)heptanoic acid, 2-[2-(methylamino)ethoxy]acetic acid, 2-[2-[2-(methylamino)ethoxy]ethoxy]acetic acid, 2-[3-(methylamino)propoxy]acetic acid, 3-[3-(methylamino)propoxy]propanoic acid, 4-[3-(methylamino)propoxy]butanoic acid, 2-[2-[2-(methylamino)ethoxy]ethoxy]ethoxy]acetic acid.

Amino alcohols 10 of general formula $NHR^1R^2-(CH_2)_b$—OH suitable to be used in the synthetic scheme displayed by Scheme 2 include, but are not limited to: 2-aminoethanol, 3-amino propan-1-ol, 4-amino butan-1-ol, 5-amino pentan-1-ol, 6-amino hexan-1-ol, 2-(2-aminoethoxy)ethanol, 2-[2-(2-aminoethoxy)ethoxy]ethanol, 2-(3-aminopropoxy)ethanol. 3-(3-aminopropoxy)propan-1-ol, 4-(3-aminopropoxy)butan-1-ol.

Example of diamines 11 of general formula $H_2N-L^e-NR^1R^2$ that are commercially available include, but are not limited to ethylenediamine; 1,3 diaminopropane; N-methylethylenediamine; 1,4-diaminobutane; 3-(methylamino)-propylamine; N,N'-dimethylethylenediamine; N-ethylethylenediamine; 3-(dimethylamino)-1-propylamine; N-isopropyl-ethylenediamine; N-propylethylenediamine; hexamethylenediamine; 1,2-diaminocyclohexyne; 1,4-diaminocyclohexane; and N-hexylethylenediamine.

The skilled person will appreciate that by applying steps b-e of the synthetic procedure described in Scheme 2 and if necessary an appropriate deprotection step to a carboxylic acid of general formula $PG^2S-L^2CO_2H$, $HC\equiv C-L^2-CO_2H$, $CH_2=CH-L^2-CO_2H$, $N_3-L^2-CO_2H$ or $PG^3=C-L^2CO_2H$, wherein $PG^2$ is a sulfhydryl protecting group (e.g. benzyl) and $PG^3$ is an aldehyde protecting group (e.g. dithiane or acetal) analogues 7a, 7b, 7c, 7d and 7e will be accessed.

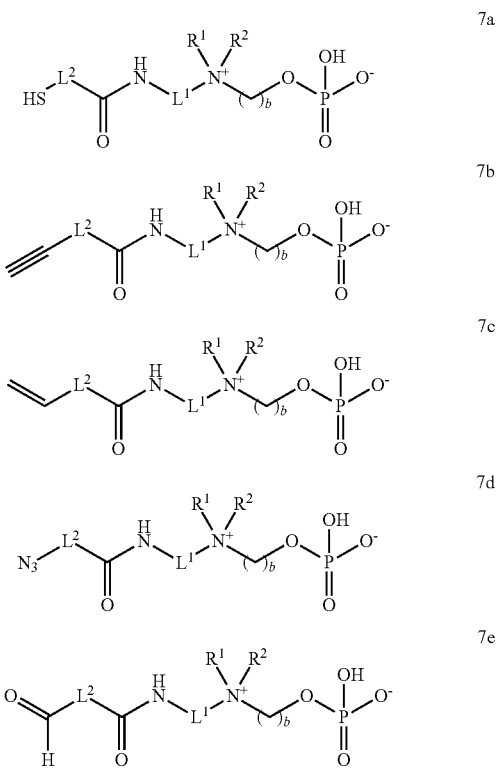

Example of suitable carboxylic acids to be used as starting material for obtaining analogues 7a-7e include, but are not restricted to: 6-thiohexanoic acid, 6-azidohexanoic acid, 5-thiopentanoic acid, 5-azidopentanoic acid, 4-thiobutanoic acid, 4-azidobutanoic acid, 3-thiopropanoic acid, 3-azidopropanoic acid, thioacetic acid, 3-butynoic acid, 4-pentynoic acid.

A.3 Alternatively, diamines of general formula $R^3HN-L^4-NR^1R^2$ (20) can be successfully used for accessing compounds of general formula I, wherein X represents —$NHR^3$, $R^3$ is selected from: —H, —$CH_3$, —$C_2H_5$, —$C_3H_7$ and -L- represents -$L^a$- (see Scheme 3). Diamines 20 can be commercially available (e.g. N,N-dimethyl-1,3-propanediamine) or can be easily obtained for example starting from the corresponding halogeno derivatives via a two steps synthetic including conversion of the halogeno derivatives to the azido derivatives and reduction of the azido derivatives to the corresponding primary amines.

Starting from diamines 20 of general formula of general formula $R^3HN-L^4-NR^1R^2$, the compounds of general formula 24 can be accessed in four steps including protection of the primary of secondary amine with protecting group $PG^1$ wherein $PG^1$ has the meaning defined at paragraph A.1, quaternization of the tertiary amine by treatment with an appropriate 2-hydroxyethyl or 3-hydroxypropyl derivative, followed by phosphorylation and deprotection of the primary or secondary amine.

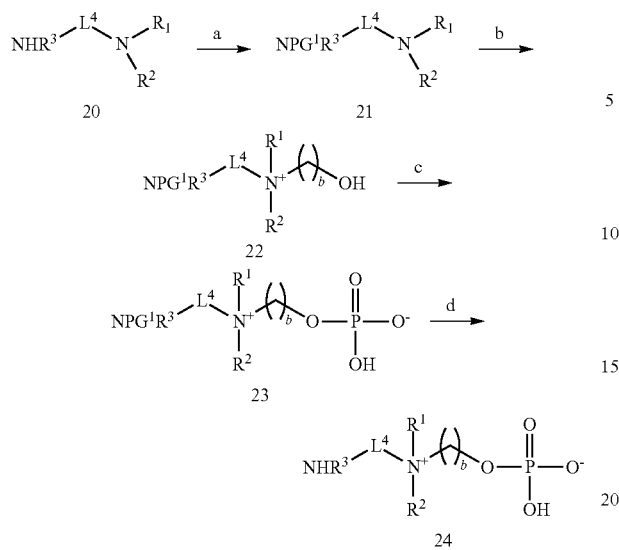

Scheme 3: Synthesis of compounds of general formula 24: a. protection amino group; b. quaternization; c. phosphorylation; d. deprotection.

B. Preparation of the Separation Material of General Formula (II)

The separation material of general formula (II) can be prepared by coupling the compounds of general formula (I) with a solid support A functionalized with a moiety -L*-FG, wherein FG is a functional group that is suitable to react with the functional group X. Examples of FG groups include —CHO, —C≡CH, —N$_3$, —CH=CH$_2$, —NH$_2$, —SH, epoxide, tresyl. Scheme 4 summarizes different coupling methodologies that can be employed to access the separation materials of general formula (II). Preferably, the compounds of general formula (I), wherein X is selected from —SH, —OH, and —NHR$^3$ are coupled to a solid support A via epoxide ring opening (see Scheme 5 a, b).

In one embodiment of the invention, the coupling of compounds of general formula (I), wherein X=—C≡CH, —N$_3$, or —CH=CH$_2$ and the solid support takes place with the formation of a triazole moiety (see Scheme 5 c, d, e). The formation of triazoles from an azide and an alkyne, also known as the alkyne azide Huisgen cycloaddition, is carried out as a 1,3-cycloaddition. A notable variant of the Huisgen 1,3-dipolar cycloaddition is the copper(I) catalyzed variant, in which organic azides and terminal alkynes are united to afford 1,4-regioisomers of 1,2,3-triazoles as sole products. This reaction is termed the copper(I)-catalyzed Azide-Alkyne Cycloaddition (CuAAC). The reaction can be performed using commercial sources of copper(I) such as cuprous bromide or iodide. However, the reaction works much better using a mixture of copper (II) (e.g. copper(II) sulfate) and a reducing agent (e.g. sodium ascorbate) to produce in situ Cu(I). As Cu(I) is unstable in aqueous solvents, stabilizing ligands are effective for improving the reaction outcome, especially if tris-(benzyltriazolylmethyl) amine (TBTA) is used. The reaction can be run in a variety of solvents and mixtures of water and a variety of (partially) miscible organic solvents including alcohols, DMSO, DMF, t-BuOH, dioxane, acetone and mixtures thereof. In addition, the reaction can be catalyzed by ruthenium. The ruthenium-catalyzed 1,3-dipolar azide-alkyne cycloaddition (RuAAC) gives 1,5-triazoles. Thus, using azide-alkyne cycloaddition separation materials of general formula (II), wherein Y is selected from:

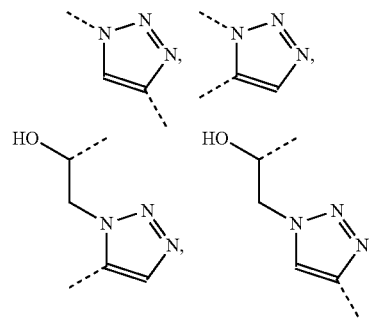

can be easily obtained.

In the same manner, separation materials of general formula (II), wherein Y is selected from:

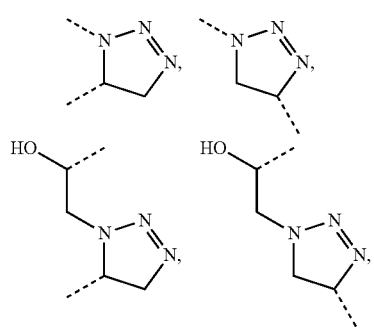

can be obtained starting from azides and alkenes.

Separation materials of general formula (II), wherein Y is selected from —CH$_2$—NH—, and —NH—CH$_2$— can be prepared by reductive amination using for example NaBH$_4$ as reductant, starting from compounds of general formula (I), wherein X is —NH$_2$ or —CH(O) and solid supports functionalized A with a moiety -L*-FG, wherein functional group FG represents —CH(O) and —NH$_2$, respectively (see Scheme 4 f, g).

Compounds of general formula (I), wherein X=—CH=CH$_2$ can be immobilized to the solid support via metathesis or Wittig reaction to provide separation materials of general formula (II), wherein Y is selected from:

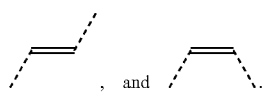

Compounds of general formula (I), wherein X=—CH=CH$_2$ or —SH can be immobilized to the solid support via thiol-ene chemistry to provide separation materials of general formula (II), wherein Y represents —S—CH$_2$—CH$_2$— or —CH$_2$—CH$_2$—S—.

Scheme 5. Coupling methodologies of the compounds of general formula (I) to a solid support.

a.

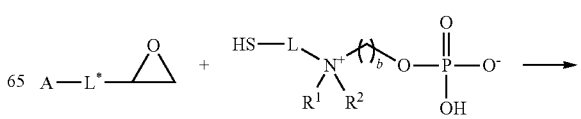

-continued

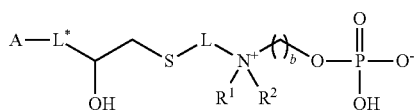

b.

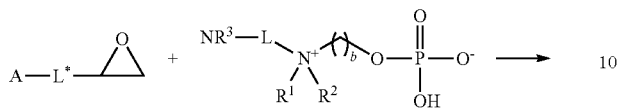

c.

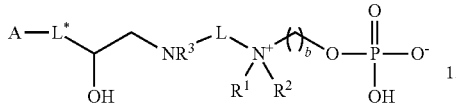

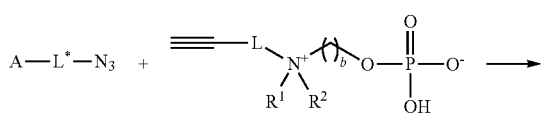

d.

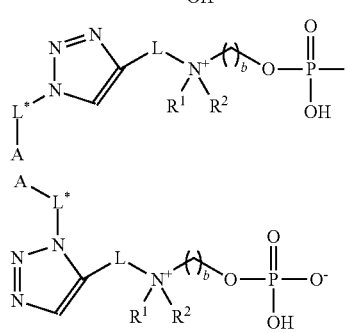

e.

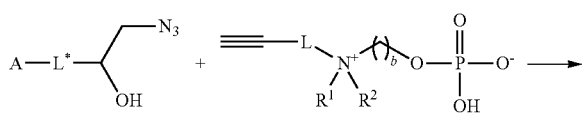

-continued

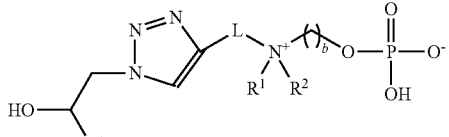

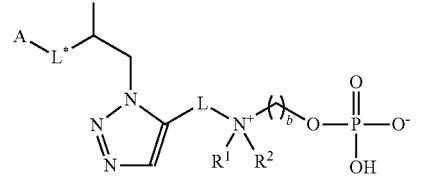

f.

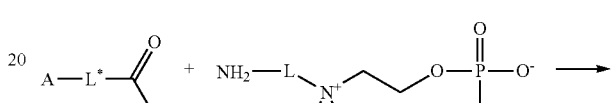

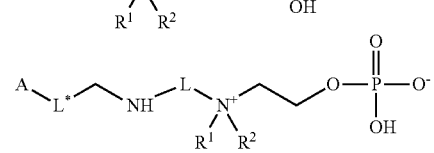

g.

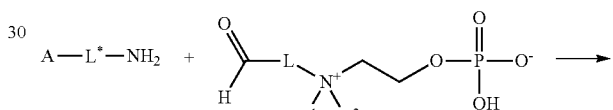

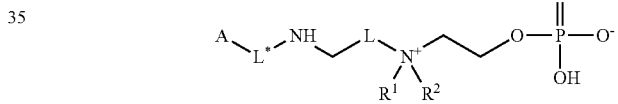

The following examples are included to demonstrate preferred embodiments of the invention. It should be appreciated by those of skill in the art that the techniques disclosed in the following examples represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

Example 1: Synthesis of benzyl N-[3-(dimethylamino)propyl]carbamate (1*)

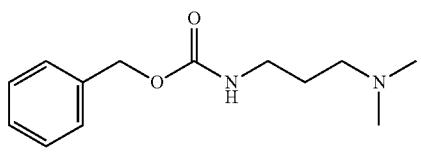 [SMILES: CN(C)CCCNC(=O)OCc1ccccc1]

To a stirred solution of N-(benzyloxycarbonyloxy)succinimide (68.8 g, 0.276 mol) in chloroform (300 ml) under argon atmosphere and at 0° C. was added drop wise N',N'-dimethylpropane-1,3-diamine (24.52 g, 0.24 mol) dissolved in chloroform (150 ml) while keeping the reaction mixture temperature at 0° C. The reaction mixture was stirred at 0° C. for 2 h, then was diluted with chloroform (400 ml) and washed with saturated aqueous sodium hydrogen carbonate (3×200 ml) and saturated sodium chloride (2×200 ml). The organic phase was dried over anhydrous magnesium sulfate, filtered and concentrated in vacuum to give 56 g (98.7%) of viscous oil as the desired product 1*, which was used as such for the next reaction. MS m/z 236.31 (M+H)$^+$ (236.15 calculated).

Example 2: Synthesis of 3-(benzyloxycarbonylamino)propyl-(2-hydroxyethyl)-dimethyl-ammonium Bromide (2*)

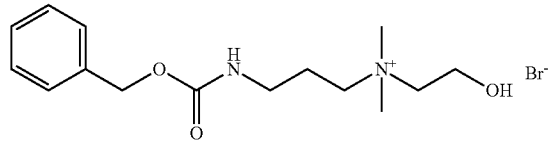 [SMILES: C[N+](C)(CCO)CCCNC(=O)OCc1ccccc1 ; [Br-]]

To an approximately 1 M solution of benzyl N-[3-(dimethylamino)propyl]carbamate (1*, 56 g, 0.237 mol, example 1) in acetonitrile, 2-bromoethanol (32.58 g, 0.261 mol) was added and the reaction mixture was incubated at room temperature until all benzyl N-[3-(dimethylamino)propyl] carbamate consumed (monitored by LC/MS and TLC). To the resulting solution of 3-(benzyloxycarbonylamino)propyl-(2-hydroxyethyl)-dimethyl-ammonium bromide five volumes of methyl tert-butyl ether were added. The muddy mixture solutions were stirred until phase separation was observed. The upper organic phase was separated from 3-(benzyloxycarbonylamino)propyl-(2-hydroxyethyl)-dimethyl-ammonium bromide by decantation and the precipitation was repeated again three more times. Finally, the target compound was obtained after pumping out the trace solvent in vacuum as viscous oil (76.7 g, 89.6% as bromide salt). Target product 2* was homogeneous by LC/MS and TLC, and was used in the phosphorylation step with no further purification. MS m/z 281.33 M$^+$ (281.19 calculated).

Example 3: Synthesis of 6-(benzyloxycarbonylamino)hexanoic acid (3*)

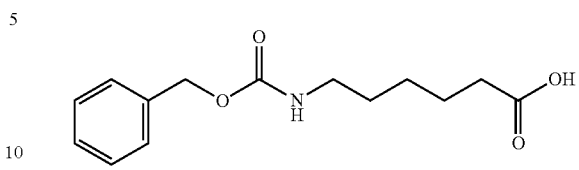

To a stirred suspension of finely powdered 6-aminocaproic acid (32.79 g, 0.25 mol) in dichloromethane (500 ml), triethylamine (63.24 g, 0.625 mol) was added. Then, trimethylchlorosilane (54.32 g, 0.5 mol) was added dropwise with vigorous stirring and the resulting mixture was refluxed for 2 h. The reaction mixture was then cooled on an ice bath and benzyl chloroformate (95%, 53.31 g, 0.313 mol) was added. The resulting mixture was stirred on ice for 60 min and at room temperature for 4 h. After removal of the solvent, the residue was distributed between 1000 ml of 4% (v/w) solution of sodium hydrogen carbonate and 500 ml of methyl tert-butyl ether. The aqueous layer was separated, acidified to pH 2.0 with 2N hydrochloric acid and extracted three times with ethyl acetate. The combined organic layers were dried over anhydrous magnesium sulfate, filtered and concentrated to yield clear oil (62.4 g, 94.1%) corresponding to target carboxylic acid 3* that was homogeneous by LC/MS and TLC, and was used in the next step with no further purification. MS m/z 265.33 (M+1)$^+$ (265.13 calculated).

Example 4: Synthesis of benzyl N-[6-[3-(dimethylamino)propylamino]-6-oxo-hexyl]carbamate (4*)

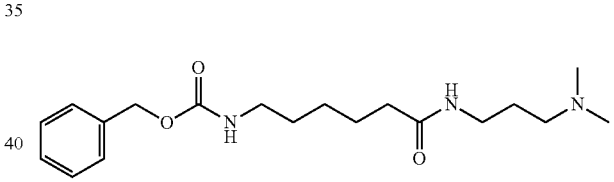

To a solution of 6-(benzyloxycarbonylamino)hexanoic acid (3*, 66.3 g, 0.25 mol, example 3) in dry dichloromethane (500 ml), a catalytic amount of dimethylformamide (1.25 ml) was added and the reaction mixture was cooled to 0° C. on ice/salt bath. A solution of oxalyl chloride (38.08 g, 0.3 mol) in dichloromethane (150 ml) was added slowly with keeping the reaction mixture temperature at 0° C. The reaction mixture was stirred for 2 h at room temperature. The volatiles were evaporated under vacuum and the residue was dissolved in dry dichloromethane (500 ml). The resulting solution was cooled to 0° C. on ice/salt bath and a mixture of N,N-dimethyl-1,3-propanediamine (25.55 g, 0.25 mol) and triethylamine (55.65 g, 0.55 mol) was added dropwise with stirring and cooling during 2 h. The reaction mixture was stirred for 6 h and the progress of the reaction was monitored by TLC and LC-MS. The precipitate was filtered, washed with a small volume of dichloromethane. Then, the dichloromethane solution was washed sequentially with saturated sodium hydrogen carbonate, saturated sodium chloride, dried over anhydrous magnesium sulfate and concentrated to give benzyl N-[6-[3-(dimethylamino)propylamino]-6-oxo-hexyl]carbamate (4*, 76.4 g, 87.4%) as a clear yellowish oil. The crude material was pure by LC/MS and TLC, and was used in the next step with no further purification. MS m/z 249.13 (M+1)$^+$ (349.24 calculated).

Example 5: Synthesis of 3-[6-(benzyloxycarbonylamino)hexanoylamino]propyl-(2-hydroxyethyl)-dimethyl-ammonium Bromide (5*)

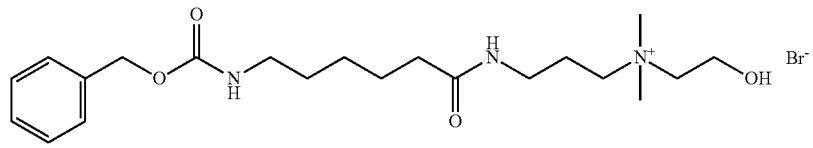 [SMILES: C[N+](C)(CCO)CCCNC(=O)CCCCCNC(=O)OCc1ccccc1 ; [Br-]]

To an approximately 1 M solution of benzyl N-[6-[3-(dimethylamino)propylamino]-6-oxo-hexyl]carbamate (4*, 56 g, 0.16 mol, example 4) in acetonitrile, 2-bromoethanol (22.03 g, 0.176 mol) was added and the reaction mixture was stirred at room temperature until all benzyl N-[6-[3-(dimethylamino)propylamino]-6-oxo-hexyl]carbamate was consumed (monitored by LC/MS and TLC). To the resulting solution of 3-[6-(benzyloxycarbonylamino)hexanoylamino]propyl-(2-hydroxyethyl)-dimethyl-ammonium bromide five volumes of methyl tert-butyl ether were added. The muddy mixture solutions were stirred until phase separation was observed. The upper organic phase was separated from 3-[6-(benzyloxycarbonylamino)hexanoylamino]propyl-(2-hydroxyethyl)-dimethyl-ammonium bromide by decantation and the precipitation was repeated again three more times. Finally, the target compound was obtained after pumping out the trace solvent in vacuum as viscous oil (5*, 66.3 g, 87.2% as bromide salt). The product was homogeneous by LC/MS and TLC, and was used in the phosphorylation step with no further purification. MS m/z 394.1 M+ (394.27 calculated).

Example 6: Synthesis of benzyl N-[2-(2-hydroxyethoxy)ethyl]carbamate (6*)

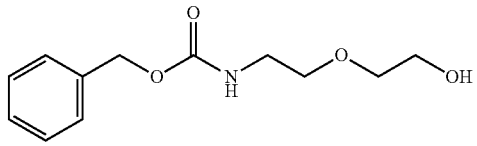 [SMILES: O=C(NCCOCCO)OCc1ccccc1]

2-(2-aminoethoxy)ethanol (25.23 g, 0.240 mol) was dissolved in 530 mL of 10% triethylamine in MeOH (48 ml, 0.345 mol of triethylamine, 480 ml of methanol) and cooled to 0° C. Benzyl chloroformate (technical grade, 95%, 34.4 ml, 0.229 mol) was added all at once, and the reaction was allowed to warm to room temperature. After 12 h, the solvent was removed by evaporation, and the product purified using silica column chromatography (ethyl acetate/hexane), resulting in a colorless oil (6*, 52 g, 0.163 mol, 95% based on benzyl chloroformate). The crude material was analytically pure as analyzed by LC/MS and TLC, and was used in the next step with no further purification. MS m/z 239.17 (M+1)+ (239.12 calculated).

Example 7: Synthesis of benzyl N-[6-[2-(2-hydroxyethoxy)ethylamino]-6-oxo-hexyl]carbamate (7*)

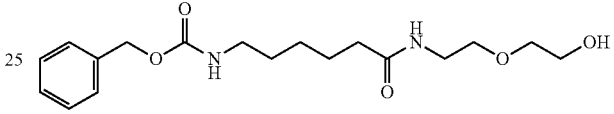

A solution of trimethyl phosphite (12.5 g, 0.101 mol) in dichloromethane (290 ml) was cooled on ice/salt bath. Then, powdered iodine (25.6 g, 0.101 mol) was added portionwise while keeping the reaction mixture temperature at 0° C. After the solid iodine was completely dissolved, 6-(benzyloxycarbonylamino)hexanoic acid (3*, 25.5 g, 0.096 mol, example 3) and triethylamine (23.3 g, 0.23 mol) were added in sequential order, and the resulting solution was stirred for 20 min in the cooling bath at 0° C. 2-(2-aminoethoxy)ethanol (10.6 g, 0.101 mol) dissolved in dichloromethane (50 ml) was added and the reaction mixture was stirred at 0° C. for 30 min. After removal of the cooling bath, the reaction mixture was stirred overnight at room temperature. The progress of the reaction was monitored by TLC and LC/MS. Then, the reaction mixture was washed sequentially with 10% (v/w) sodium hydrogen sulfate, saturated sodium chloride, saturated sodium hydrogen carbonate and dried over anhydrous magnesium sulfate. The solvent was removed by evaporation, and the product purified using silica column chromatography (ethyl acetate/hexane), resulting in a colorless oil (34.7 g, 0.091 mol, 95.1% based on 6-(benzyloxycarbonylamino)hexanoic acid). The crude material 7* was pure by LC/MS and TLC, and was used in the next step with no further purification. MS m/z 352.42 (M+H)+ (352.20 calculated).

Example 8: Synthesis of 2-[2-[6-(benzyloxycarbonylamino)hexanoylamino]ethoxy]ethyl Methanesulfonate (8*)

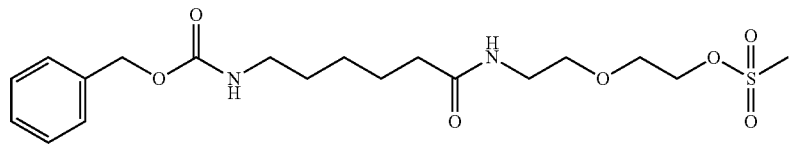 [SMILES: CS(=O)(=O)OCCOCCNC(=O)CCCCCNC(=O)OCc1ccccc1]

A solution of benzyl N-[6-[2-(2-hydroxyethoxy)ethylamino]-6-oxo-hexyl]carbamate (7*, 17.25 g, 0.049 mol, example 7) in methylene chloride (115 ml) under argon was cooled in an ice-salt bath to −5° C. Triethylamine (8.2 ml, 0.059 mol) was added and the resulting solution was stirred at −5° C. for 10 min. Methanesulfonyl chloride (4.5 ml, 0.059 mol) was added dropwise while keeping the temperature of the reaction mixture between 0° C. and −5° C. After the addition was finished, the reaction was warmed to room temperature. After 4 h, the reaction mixture was washed with water, saturated sodium chloride, and again with water. The organic phase was dried over anhydrous sodium sulfate, filtered and concentrated in vacuum. The crude material 8* was pure by LC/MS and TLC, and was used in the next step with no further purification. MS m/z 430.52 (M+H)+ (430.18 calculated).

Example 9: Synthesis of 2-[2-[6-(benzyloxycarbonylamino)hexanoylamino]ethoxy]ethyl-(2-hydroxyethyl)-dimethyl-ammonium Methanesulfonic Acid Salt (9*)

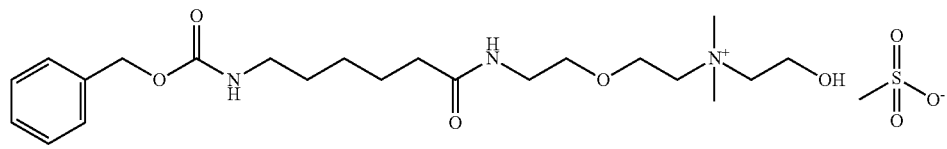

To 1 M solution of 2-[2-[6-(benzyloxycarbonylamino)hexanoylamino]ethoxy]ethyl methanesulfonate (8*, 18.6 g, 0.043 mol, example 8) in acetonitrile, 2-(dimethylamino)ethanol (4.24 g, 0.048 mol) was added over 20-30 minutes. After the addition was completed, the resulting solution was refluxed with continuous stirring until all alkyl mesylate was consumed. The progress of the reaction was monitored by LC/MS and TLC. After 12 h, the reaction mixture was cooled down and acetonitrile was evaporated in vacuum. The resulting mixture was dissolved in 200 ml of hot methyl tert-butyl ether. The solution was allowed to cool slowly to room temperature and then allowed to stand 12 h at 0-5° C. until crystallization was completed. Approximately 19.7 g (87.7% as methanesulfonic acid salt) of a white solid corresponding to target alcohol 9* was recovered. The crude material was pure by LC/MS and TLC, and was used in the next step with no further purification. MS m/z 424.55 M+ (424.28 calculated).

Example 10: Synthesis of 6-(1,3-dioxoisoindolin-2-yl)hexanoic acid (10*)

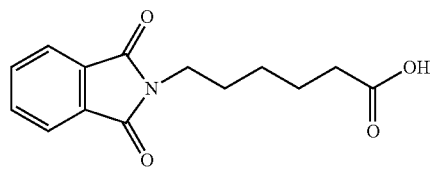 [SMILES: O=C(O)CCCCCN1C(=O)c2ccccc2C1=O]

A stirred mixture of 6-aminocaproic acid (65.6 g, 0.5 mol), phthalic anhydride (74.1 g, 0.5 mol), and acetic acid (115 ml) was heated to reflux for 9 h. The product that crystallized on cooling was isolated by filtration, washed several times with water, and dried in vacuum at 100° C. to obtain 124.2 g (95.1%) of 6-(1,3-dioxoisoindolin-2-yl)hexanoic acid 10* that was homogeneous by LC/MS and TLC, and was used in the next step with no further purification. MS m/z 261.24 (M+H)+ (261.10 calculated).

Example 11: Synthesis of 2-[2-(2-hydroxyethoxy)ethyl]isoindoline-1,3-dione (11*)

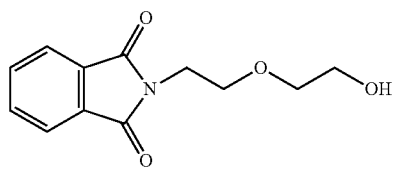 [SMILES: O=C1c2ccccc2C(=O)N1CCOCCO]

A 1 L three-neck round bottom flask equipped with a mechanical stirrer, a nitrogen inlet-outlet, and a Dean-Stark trap topped by a reflux condenser was charged a solution of phthalic anhydride (88.87 g, 0.6 mol) and 2-(2-aminoethoxy)ethanol (63.08 g, 0.6 mol) in toluene (540 ml). The reaction mixture was refluxed until 1 equiv of water was collected in the Dean-Stark trap (approximately 24 h). After 24 h toluene was removed under vacuum and the residue was dissolved in ethyl acetate (550 ml) and washed sequentially with 10% (v/w) sodium hydrogen sulfate, saturated sodium chloride, saturated sodium hydrogen carbonate and dried over anhydrous magnesium sulfate. The solvent is removed under vacuum and the residue was crystallized from methyl tert-butyl ether. Approximately 130 g (92.1%) of a white solid corresponding to target alcohol 11* was recovered. The crude material was pure by LC/MS and TLC, and was used in the next step with no further purification. MS m/z 235.27 (M+H)+ (235.08 calculated).

Example 12: Synthesis of 2-[2-(1,3-dioxoisoindolin-2-yl)ethoxy]ethyl Methanesulfonate (12*)

This example illustrates a method for preparation of methanesulfonate ester of N-protected 2-(2-aminoethoxy)ethanol.

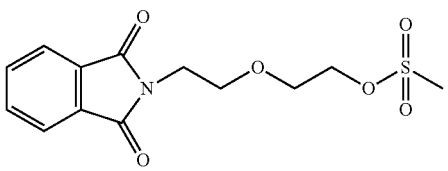 [SMILES: CS(=O)(=O)OCCOCCN1C(=O)c2ccccc2C1=O]

A solution of 2-[2-(2-hydroxyethoxy)ethyl]isoindoline-1,3-dione (11*, 47.05 g, 0.2 mol, example 11) in methylene chloride (300 ml) under argon was cooled in an ice-salt bath to −5° C. Triethylamine (33.4 ml, 0.24 mol) was added and the resulting solution was stirred at −5° C. for 10 min. Methanesulfonyl chloride (18.6 ml, 0.24 mol) was added drop wise while keeping the temperature of the reaction mixture between 0° C. and −5° C. After the addition was finished, the reaction was warmed to room temperature. After 4 h, the reaction mixture was washed with water, saturated sodium chloride, and again with water. The organic phase was dried over anhydrous sodium sulfate, filtered and concentrated in vacuum. The crude material was pure by LC/MS and TLC, and was used in the next step with no further purification. MS m/z 313.17 (M+H)+ (313.06 calculated).

Example 13: Synthesis of 2-[2-(1,3-dioxoisoindolin-2-yl)ethoxy]ethyl-(2-hydroxyethyl)-dimethyl-ammonium Methanesulfonic Acid Salt (13*)

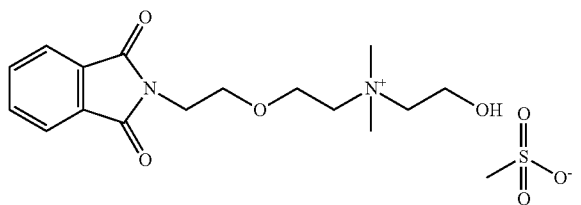

To an approximately 1 M solution of 2-[2-(1,3-dioxoisoindolin-2-yl)ethoxy]ethyl methanesulfonate (12*, 32.53 g, 0.104 mol, example 12) in acetonitrile 2-(dimethylamino)ethanol (10.18 g, 0.114 mol) was added over 20-30 minutes. After the addition was completed, the resulting solution was refluxed with continuous stirring until all alkyl mesylate was consumed. The progress of the reaction was monitored by LC/MS and TLC. After 12 h, the reaction mixture was cooled down and the acetonitrile was evaporated in vacuum. The resulting mixture was dissolved in 150 ml of hot acetonitrile and to the resulting solution were subsequently added 200 ml of hot methyl tert-butyl ether. The solution was allowed to cool slowly to room temperature and then allowed to stand overnight at 0-5° C. until crystallization was completed. Approximately 50.7 g (92.6% as methanesulfonic acid salt) of a white solid was recovered. The crude material corresponding to the target compound 13* was pure by LC/MS and TLC, and was used in the next step with no further purification. MS m/z 307.07 M+ (307.17 calculated).

Example 14: Synthesis of 2-[2-(1,3-dioxoisoindolin-2-yl)ethoxy]ethyl-(3-hydroxypropyl)-dimethyl-ammonium Methanesulfonic Acid Salt (14*)

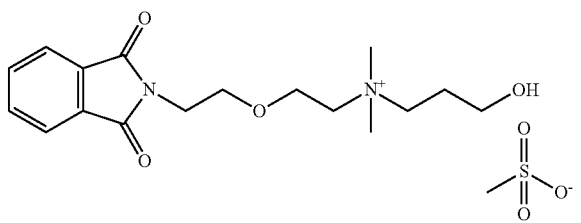

To an approximately 1 M solution of 2-[2-(1,3-dioxoisoindolin-2-yl)ethoxy]ethyl methanesulfonate (12*, 30.41 g, 0.097 mol, example 12) in acetonitrile 3-(dimethylamino)propan-1-ol (11.01 g, 0.107 mol) was added. The addition of the 3-(dimethylamino)propan-1-ol was taken somewhere between 20-30 minutes. When everything was added, the resulting solution was refluxed with continuous stirring until all alkyl mesylate was consumed. The progress of the reaction was monitored by LC/MS and TLC. After 12 h, the reaction mixture was cooled down and the acetonitrile was evaporated in vacuum. The resulting mixture was dissolved in 120 ml of hot acetonitrile and to the resulting solution were subsequently added 200 ml of hot methyl tert-butyl ether. The solution was allowed to cool slowly to room temperature and then allowed to stand overnight at 0-5° C. until crystallization was completed. Approximately 46.1 g (88.1%) of a white solid was recovered. The crude material corresponding to target compound 14* was pure by LC/MS and TLC, and was used in the next step with no further purification. MS m/z 321.11 M+ (321.18 calculated).

Example 15: Epoxy-Activation of Sepharose 6B

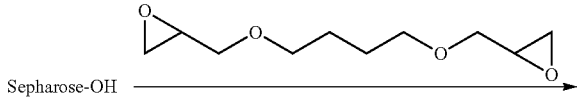

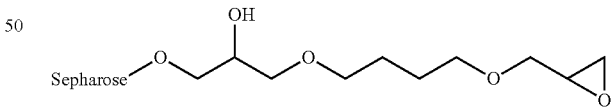

Sepharose 6B (GE Healthcare Life Sciences) was washed on a glass filter-funnel with 3×1000 ml portions of water and suction-dried. Then one hundred gram of suction-dried Sepharose 6B was mixed with 100 ml of 1,4-butanediol diglycidyl ether (CAS N° 2425-79-8) and 100 ml of 0.6 M sodium hydroxide solution containing 2 mg of sodium borohydride per milliliter. The suspension was mixed by rotation for 8 h at room temperature and the reaction was stopped by washing of the gel on a glass filter-funnel with 10×400 ml portions of hot (40-60° C.) water. The oxirane content of the gel was 67 μmol/g of suction-dried gel.

Example 16: Assay for Determining the Number of Epoxy-Groups

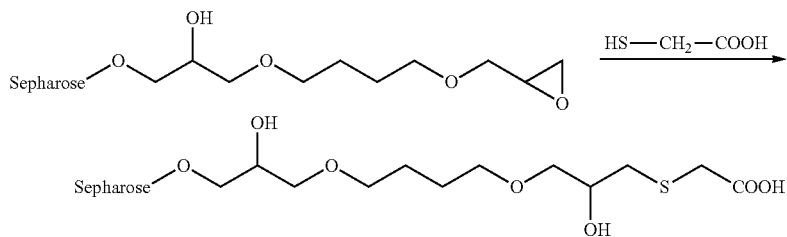

The epoxy-activated Sepharose 6B is reacted with mercaptoacetic acid and the number of acidic groups introduced is determined by titration according to a method described in Scoble, J A and Scopes, R K *Journal of Chromatography A*, 1996, 752, 67.

Example 17: Synthesis of Azide-Functionalized Sepharose 6B

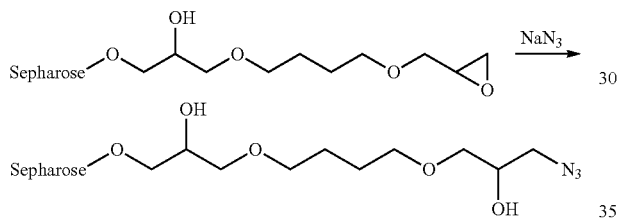

Ten grams of suction-dried epoxy-activated Sepharose 6B (example 15) was added into a 50 ml 1 M solution of sodium azide in water. The mixture was incubated on a laboratory rotating mixer 24 h at room temperature. The gel was washed with 4×100 ml of water and kept in 20% (v/v) ethanol until further use.

Example 18: Assay for Determining the Number of Azido-Groups

Azido groups of azido Sepharose 6B were quantitatively reduced to amino groups by reaction with DTT (Handlon, A L and Oppenheimer, N J, *Pharmaceutical Research* 1988, 5, 297.) and the resulting amino groups were quantified with TNBS according to published procedure (Antoni, G et al. *Analytical Biochemistry* 1983, 129, 60). The method is based on the reaction of the matrix with excess 2,4,6-trinitrobenzenesulfonic acid (TNBS) and subsequent quantitative determination of unreacted TNBS by reaction with glycine.

Example 19: Determination of Free Primary Amino Groups by Spectrophotometric Method The amount of primary amino groups was directly quantitated using a standard curve generated after reaction of L-glutamic acid with o-phthaldehyde and N-acetyl-L-cysteine at room temperature and pH 9.5 (Medina Hernandez, M J et al. *Microchemical Journal* 1990, 42, 288). N-acetyl-L-cysteine derivatives are highly stable and not requiring a strict control of the time of reaction unlike to 2-metcaptoethanol. The relationship between UV absorbance at 335 nm and concentration of amino-groups was found to be linear.

Example 20: Determination of Free Secondary Amino Groups by Spectrophotometric Method The amount of secondary amino groups was directly quantitative estimated using the reaction of this group of

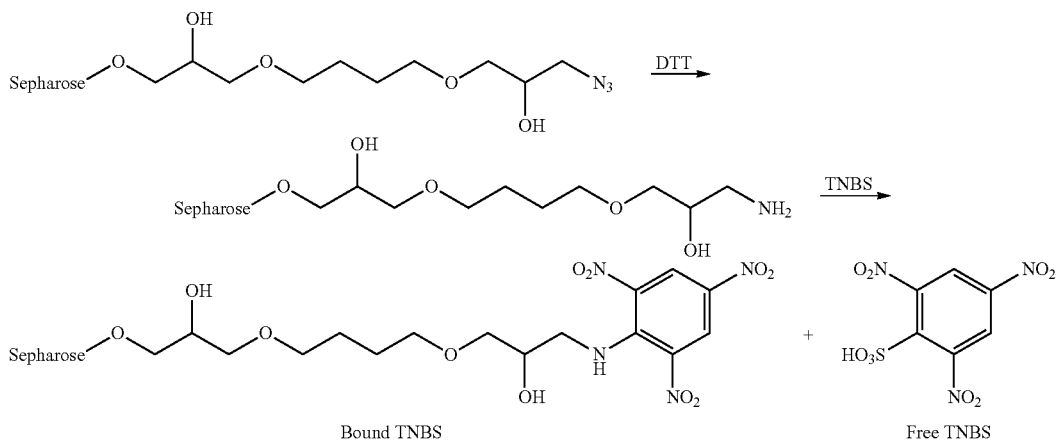

Bound TNBS        Free TNBS compounds with sodium nitroprusside and acetaldehyde (Lin, C M L and Wagner, C *Analytical Biochemistry* 1974, 60, 278).

Example 21: Immobilization of 2-[3-aminopropyl(dimethyl)ammonio]ethyl Hydrogen Phosphate On Epoxy-Activated of Sepharose 6B (Separation Material 1)

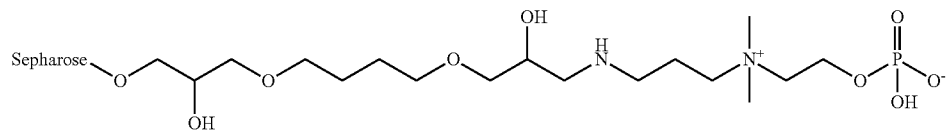

Phosphorylation.

To 0.2 M solution of phosphorus oxychloride (3.7 g) in dry acetonitrile, kept at between 0° C. and −10° C., was added triethylamine (2.68 g). After addition of triethylamine, an approximately 0.2 M solution of 3-(benzyloxycarbonylamino)propyl-(2-hydroxyethyl)-dimethyl-ammonium bromide (2*, 5.81 g, example 2) was added dropwise over a time range of 30 min, while keeping the temperature of the reaction mixture between 0° C. and −5° C. After the addition was finished the suspension was incubated for additional 24 h at room temperature. The progress of the reaction was monitored by LC/MS and TLC. The triethylamine hydrochloride precipitate was filtered and to the resulting solution was added water (1.8 ml) under stirring, while keeping the temperature at 0-5° C. Removal of water-solvent mixture in vacuum gave the phosphorylated product, which was pure enough for subsequent deprotection and immobilization.

Protecting Group Cleavage

To a stirred solution of above phosphorylated product in water (50 ml) was added 10% palladium on activated charcoal (10 mol %) at 25° C. The resulting mixture was stirred for 24 h at 25° C. under $H_2$ (1 atm) and then filtered. The catalyst was washed with water (2×10 ml) and the clear solution was concentrated under reduced pressure to give 2-[3-aminopropyl(dimethyl)ammonio]ethyl hydrogen phosphate with high purity after filtration.

Immobilization.

Twenty grams of suction-dried epoxy-activated Sepharose 6B (example 15) were added into a solution of 2-[3-aminopropyl(dimethyl)ammonio]ethyl hydrogen phosphate (40 ml). pH of the resulting suspension was adjusted to 11.0 with 1 M sodium hydroxide solution. The mixture was incubated on a laboratory rotating mixer 24 h at room temperature. The gel was washed with 4×100 ml of autoclaved water and kept in 20% (v/v) ethanol until further use.

Example 22: Immobilization of 2-[3-(6-aminohexanoylamino)propyl-dimethyl-ammonio]ethyl Hydrogen Phosphate On Epoxy-Activated of Sepharose 6B (Separation Material 2)

Phosphorylation.

To an approximately 0.2 M solution of phosphorus oxychloride (3.7 g) in dry acetonitrile, kept at between 0° C. and −10° C., was added triethylamine (2.68 g). After addition of triethylamine, an approximately 0.2 M solution of 3-[6-(benzyloxycarbonylamino)hexanoylamino]propyl-(2-hydroxyethyl)-dimethyl-ammonium bromide (5*, 7.63 g, example 5) was added dropwise over a time range of 30 min while keeping the temperature of the reaction mixture between 0° C. and −5° C. After the addition was finished the suspension was incubated for additional 24 h at room temperature. The progress of the reaction was monitored by LC/MS and TLC. The triethylamine hydrochloride precipitate was filtered and the resulting solution was added water (1.8 ml) under stirring, while keeping the temperature at 0-5° C. Removal of water-solvent mixture in vacuum gave the phosphorylated product, which was pure enough for subsequent deprotection and immobilization.

Protecting Group Cleavage

To a stirred solution of above phosphorylated product in water (50 ml) was added 10% palladium on activated charcoal (10 mol %) at 25° C. The resulting mixture was stirred for 24 h at 25° C. under $H_2$ (1 atm) and then filtered. The catalyst was washed with water (2×10 ml) and the clear solution was concentrated under reduced pressure to give 2-[3-aminopropyl(dimethyl)ammonio]ethyl hydrogen phosphate with high purity after filtration.

Immobilization.

Twenty grams of suction-dried epoxy-activated Sepharose 6B (example 15) were added into a solution of 2-[3-(6-aminohexanoylamino)propyl-dimethyl-ammonio]ethyl hydrogen phosphate (40 ml). pH of the resulting suspension was adjusted to 11.0 with 1 M sodium hydroxide solution. The mixture was incubated on a laboratory rotating mixer 24 h at room temperature. The gel was washed with 4×100 ml of autoclaved water and kept in 20% (v/v) ethanol until further use.

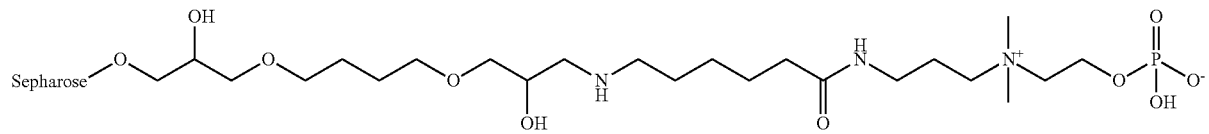

Example 23: Immobilization of 2-[2-[2-(6-amino-hexanoylamino)ethoxy]ethyl-dimethyl-ammonio]ethyl Hydrogen Phosphate On Epoxy-Activated of Sepharose 6B (Separation Material 3)

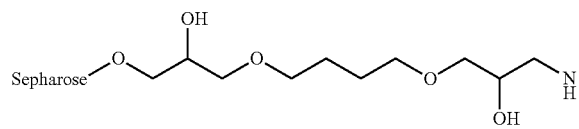

Phosphorylation.

To an approximately 0.2 M solution of phosphorus oxychloride (3.7 g) in dry acetonitrile, kept at between 0° C. and −10° C., was added triethylamine (2.68 g). After addition of triethylamine, an approximately 0.2 M solution of 2-[2-[6-(benzyloxycarbonylamino)hexanoylamino]ethoxy]ethyl-(2-hydroxyethyl)-dimethyl-ammonium methanesulfonic acid salt (9*, 8.36 g, example 9) was added dropwise over a time range of 30 min while keeping the temperature of the reaction mixture between 0° C. and −5° C. After the addition was finished the suspension was incubated for additional 24 h at room temperature. The progress of the reaction was monitored by LC/MS and TLC. The triethylamine hydrochloride precipitate was filtered and the resulting solution was added water (1.8 ml) under stirring, while keeping the temperature at 0-5° C. Removal of water-solvent mixture in vacuum gave the phosphorylated product, which was pure enough for subsequent deprotection and immobilization.

Protecting Group Cleavage

To a stirred solution of above phosphorylated product in water (50 ml) was added 10% palladium on activated charcoal (10 mol %) at 25° C. The resulting mixture was stirred for 24 h at 25° C. under $H_2$ (1 atm) and then filtered. The catalyst was washed with water (2×10 ml) and the clear solution was concentrated under reduced pressure to give 2-[3-aminopropyl(dimethyl)ammonio]ethyl hydrogen phosphate with high purity after filtration.

Immobilization.

Twenty grams of suction-dried epoxy-activated Sepharose 6B (example 15) were added into a solution of 2-[2-[2-(6-aminohexanoylamino)ethoxy]ethyl-dimethyl-ammonio]ethyl hydrogen phosphate (40 ml). The pH of the resulting suspension was adjusted to 11.0 with 1 M sodium hydroxide solution. The mixture was incubated on a laboratory rotating mixer 24 h at room temperature. The gel was washed with 4×100 ml of autoclaved water and kept in 20% (v/v) ethanol until further use.

Example 24: Immobilization of 2-[2-(2-aminoethoxy)ethyl-dimethyl-ammonio]ethyl Hydrogen Phosphate On Epoxy-Activated of Sepharose 6B (Separation Material 4)

Phosphorylation.

To an approximately 0.2 M solution of phosphorus oxychloride (3.7 g) in dry acetonitrile, kept at between 0° C. and −10° C., was added triethylamine (2.68 g). After addition of triethylamine, an approximately 0.2 M solution of 2-[2-(1,3-dioxoisoindolin-2-yl)ethoxy]ethyl-(2-hydroxyethyl)-dimethyl-ammonium methanesulfonic acid salt (6.47 g, example 13) was added dropwise over a time range of 30 min while keeping the temperature of the reaction mixture at between 0° C. and −5° C. After the addition was finished the suspension was incubated for additional 24 h at room temperature. The progress of the reaction was monitored by LC/MS and TLC. The triethylamine hydrochloride precipitate was filtered and the resulting solution was added water (1.8 ml) under stirring, while keeping the temperature at 0-5° C. Removal of water-solvent mixture in vacuum gave the phosphorylated product, which was pure enough for subsequent deprotection and immobilization.

Protecting Group Cleavage.

To a stirred solution of above phosphorylated product in water (50 ml) was added 1 M sodium hydroxide until the pH of the solution reached 11.5. The resulting mixture was stirred for 1 h at 25° C. and then 6 M hydrochloric acid was added until the pH of the solution reached 2. The resulting mixture was stirred for 12 h at 25° C. and then pH of the reaction mixture was adjusted to 7.

Immobilization.

Twenty grams of suction-dried epoxy-activated Sepharose 6B (example 15) was added into a solution of 2-[2-(2-aminoethoxy)ethyl-dimethyl-ammonio]ethyl hydrogen phosphate (40 ml). pH of the resulting suspension was adjusted to 11.0 with 1 M sodium hydroxide solution. The mixture was incubated on a laboratory rotating mixer 24 h at room temperature. The gel was washed with 4×100 ml of autoclaved water and kept in 20% (v/v) ethanol until further use.

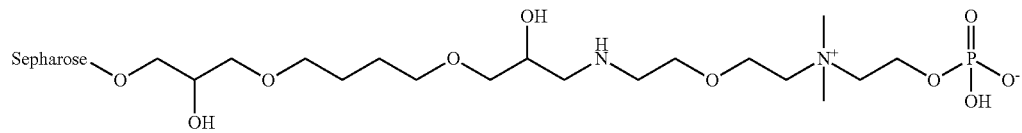

Example 25: Immobilization of 3-[2-(2-aminoethoxy)ethyl-dimethyl-ammonio]propyl Hydrogen Phosphate On Epoxy-Activated of Sepharose 6B (Separation Material 5)

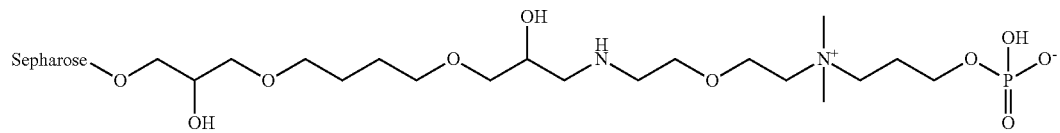

Phosphorylation.

To an approximately 0.2 M solution of phosphorus oxychloride (3.7 g) in dry acetonitrile, kept at between 0° C. and −10° C., was added triethylamine (2.68 g). After addition of triethylamine, an approximately 0.2 M solution of 2-[2-(1,3-dioxoisoindolin-2-yl)ethoxy]ethyl-(3-hydroxypropyl)-dimethyl-ammonium methanesulfonic acid salt (14*, 6.7 g, example 14) was added dropwise over a time range of 30 min while keeping the temperature of the reaction mixture at between 0° C. and −5° C. After the addition was finished the suspension was incubated for additional 24 h at room temperature. The progress of the reaction was monitored by LC/MS and TLC. The triethylamine hydrochloride precipitate was filtered and the resulting solution was added water (1.8 ml) under stirring, while keeping the temperature at 0-5° C. Removal of water-solvent mixture in vacuum gave the phosphorylated product, which was pure enough for subsequent deprotection and immobilization.

Protecting Group Cleavage

To a stirred solution of above phosphorylated product in water (50 ml) was added 1 M sodium hydroxide until pH of the solution reached 11.5. The resulting mixture was stirred for 1 h at 25° C. and then 6 M hydrochloric acid was added until pH of the solution reached 2. The resulting mixture was stirred for 12 h at 25° C. and then pH of the reaction mixture was adjusted to 7.

Immobilization

Twenty grams of suction-dried epoxy-activated Sepharose 6B (example 15) was added into a solution of 3-[2-(2-aminoethoxy)ethyl-dimethyl-ammonio]propyl hydrogen phosphate (40 ml). pH of the resulting suspension was adjusted to 11.0 with 1 M sodium hydroxide solution. The mixture was incubated on a laboratory rotating mixer 24 h at room temperature. The gel was washed with 4×100 ml of autoclaved water and kept in 20% (v/v) ethanol until further use.

Example 26: Comparative Example

Immobilization of (4-aminophenyl) 2-(trimethylammonio)ethyl phosphate on epoxy-activated of Sepharose 6B (Separation material 6).

Immobilization.

Twenty grams of suction-dried epoxy-activated Sepharose 6B (example 15) was added into a solution of (4-aminophenyl) 2-(trimethylammonio)ethyl phosphate (4.41 g in 40 ml of water). pH of the resulting suspension was adjusted to 11.5 with 1 M sodium hydroxide solution. The mixture was incubated on a laboratory rotating mixer 24 h at room temperature. The gel was washed with 4×100 ml of autoclaved water and kept in 20% (v/v) ethanol until further use.

Example 27: Determination of the Binding Affinity

Binding and washing buffer: 100 mM Tris, pH 8.0, 200 mM sodium chloride, 2 mM calcium chloride.

Elution buffer: 100 mM Tris, pH 8.0, 200 mM sodium chloride, 2 mM EDTA.

All chromatographic operations were performed at room temperature.

0.5 g of each separation material was packed into a small column and equilibrated with 12 resin bed volumes (6 ml) of binding buffer. 40-50 ml of human serum or plasma (CRP>0.1 mg/ml) was applied onto each column at 1.2 ml/min. Unbound material was washed away with 60 resin bed volumes of binding buffer (30 ml) until $OD_{280}$ reading approached to zero baseline. The affinity resin bound proteins were eluted with elution buffer at a rate of 1.2 ml/min and 3.6 ml fractions were collected. Collected fractions were stored at 4° C. until assayed by SDS-PAGE. A quantitative determination of human C-Reactive Protein (CRP) was performed by ELISA.

The results are summarized in Table 1.

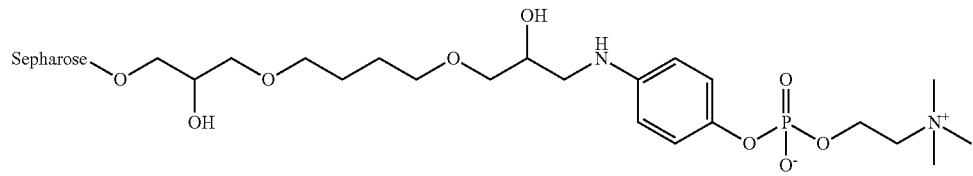

TABLE 1

| Separation material | Ligand structure | Bound CRP (mg of human CRP per 1 g of the resin) |
|---|---|---|
| Separation material 3 (example 23) | Sepharose-O-CH2-CH(OH)-CH2-O-(CH2)3-O-CH2-CH(OH)-CH2-NH-(CH2)5-C(O)-NH-CH2-CH2-O-CH2-CH2-N+(CH3)2-CH2-CH2-O-P(O)(OH)-O− | 21.7 |
| Separation material 4 (example 24) | Sepharose-O-CH2-CH(OH)-CH2-O-(CH2)3-O-CH2-CH(OH)-CH2-NH-CH2-CH2-O-CH2-CH2-N+(CH3)2-CH2-CH2-O-P(O)(OH)-O− | 16.7 |
| Separation material 5 (example 25) | Sepharose-O-CH2-CH(OH)-CH2-O-(CH2)3-O-CH2-CH(OH)-CH2-NH-CH2-CH2-O-CH2-CH2-N+(CH3)2-(CH2)3-O-P(O)(OH)-O− | 16.9 |
| Separation material 6 (example 26) | Sepharose-O-CH2-CH(OH)-CH2-O-(CH2)3-O-CH2-CH(OH)-CH2-NH-C6H4-O-P(O)(O−)-O-CH2-CH2-N+(CH3)3 | 9.1 |

The invention claimed is:

1. A separation material of general formula (II):

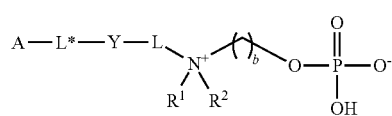

wherein b is selected from 2 and 3;

$R^1$ and $R^2$ are independently of each other selected from: —$CH_3$, —$C_2H_5$, —$C_3H_7$, —$C_4H_9$, —$C_5H_{11}$ and —$C_6H_{13}$, or $R^1$ and $R^2$ can form together with the nitrogen atom to which they are connected a heterocycle selected from:

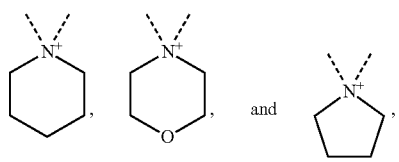

wherein one or more hydrogen atom(s) can be replaced with (a) fluorine atom(s);

Y is selected from: —CH(OH)—$CH_2$—N($R^4$)—, —CH(OH)—$CH_2$—S—, —$CH_2$—NH—, —NH—$CH_2$—, —$CH_2$—$CH_2$—S—, —S—$CH_2$—$CH_2$—,

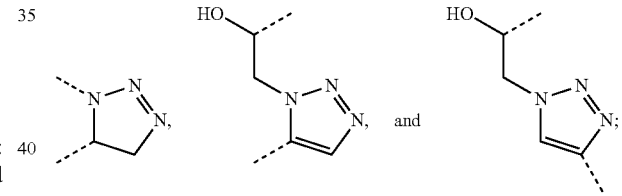

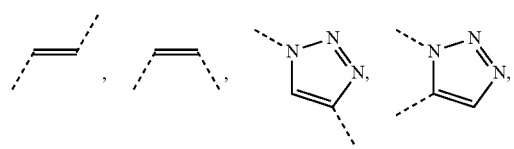

$R^4$ is selected from: —H, —$CH_3$, —$C_2H_5$, —$C_3H_7$ and —C(O)—$CH_3$;

-L- is selected from: -$L^a$-, -$L^a$-$L^e$-, -$L^a$-$L^b$-$L^e$- and -$L^a$ $L^b$ $L^d$ $L^c$ $L^e$-, wherein -$L^a$- is selected from: —($CH_2$)$_m$—, —($CH_2$—$CH_2$—O)$_m$—$CH_2$—,

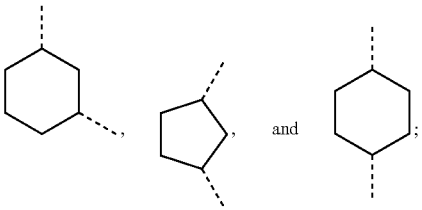

-$L^b$- and -$L^c$- are independently of each other selected from: —O—, —NH—C(O)—, —C(O)—NH—, —O—C(O)—NH— and —$SO_2$—;

-$L^d$-is selected from: —($CH_2$)$_n$—, —($CH_2$—$CH_2$—O)$_n$—$CH_2$—,

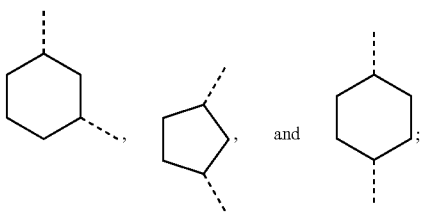

-L$^e$- is selected from: —(CH$_2$)$_{p1}$—, —(CH$_2$)$_{p1}$—O—(CH$_2$)$_{p2}$—,

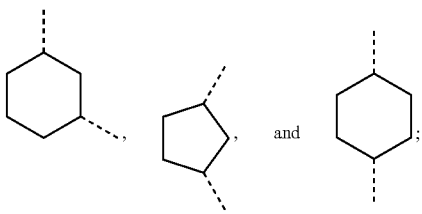

-L*- is selected from: -L*$^a$-, -L*$^a$-L*$^e$- and -L*$^a$-L*$^b$-L*$^e$-, wherein -L*$^a$- is selected from: —(CH$_2$)$_o$—, —(CH$_2$—CH$_2$—)$_o$—C$_2$H$_4$—, —(CH$_2$—CH$_2$—O)$_o$—CH$_2$— and —CH$_2$—CH(OH)—CH$_2$—;

-L*$^e$- is selected from: —(CH$_2$)$_q$—, —C$_2$H$_4$—(O—CH$_2$—CH$_2$)$_q$—, and —CH$_2$—(O—CH$_2$—CH$_2$)$_q$—;

-L*$^b$- is selected from: —O—(CH$_2$)$_r$—O—, —S—(CH$_2$)$_r$—S—, —SO$_2$—, —S—, —O—, —NH—C(O)—, —C(O)—NH— and —S—S—;

m is selected from 2, 3, 4, 5, 6, 7, 8, 9, 10; and n, p1, p2, o, r, q are independently of each other selected from 1, 2, 3, 4, 5, 6, 7, 8, 9, 10;

A is a solid support selected from the group consisting of: polyvinylpyrrolidone (PVP), polysulfone (PS), polyethersulfone (PES), polyarylethersulfone (PAES), polyacrylate, poly(methyl methacrylate) (PMMA), poly(glycidyl methacrylate) (PGMA), poly(hydroxy metacrylate), polystyrene (PS), polytetrafluoroethylene (PTFE), polyacrylamide, polyacrolein, acrylonitrile butadiene styrene (ABS), polyacrylonitrile (PAN), polyurethane (PU), a copolymer of methacrylamide and N,N'-methylen-bis(acrylamide), polyethylene glycol (PEG), hyperfluorocarbon, agarose, alginate, carrageenan, chitin, starch, cellulose, nitrocellulose, crosslinked agarose, glass, silica, kieselguhr, zirconia, alumina, iron oxide and mixtures of said solid supports; and protonated and deprotonated forms of this separation material.

2. The separation material according to claim 1, wherein the solid support A is selected from the group consisting of polysulfone (PS), polyethersulfone (PES), polyarylethersulfone (PAES), mixtures thereof.

3. A column comprising the separation material according to claim 1.

4. A device comprising the column according to claim 3.

5. A method for extracorporeal removal of CRP from a biological fluid of a patient, comprising:
a) providing a separation material of claim 1, and
b) contacting the biological fluid of the patient with the separation material.

6. The method according to claim 5, wherein the biological fluid is selected from: blood, blood plasma, peritoneal fluid and lymphatic fluid.

7. A column comprising the separation material according to claim 2.

* * * * *